(12) United States Patent
Hodgson

(10) Patent No.: US 11,400,233 B2
(45) Date of Patent: Aug. 2, 2022

(54) SHEATH REMOVAL MECHANISM

(71) Applicant: Sanofi-Aventis Deutschland GMBH, Frankfurt am Main (DE)

(72) Inventor: Louise Hodgson, Herts (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 513 days.

(21) Appl. No.: 16/222,760

(22) Filed: Jan. 14, 2019

(65) Prior Publication Data
US 2019/0117902 A1    Apr. 25, 2019

Related U.S. Application Data

(63) Continuation of application No. 15/124,790, filed as application No. PCT/EP2015/056687 on Mar. 27, 2015, now Pat. No. 10,188,802.

(30) Foreign Application Priority Data

Mar. 28, 2014 (EP) ..................................... 14162455

(51) Int. Cl.
*A61M 5/32* (2006.01)

(52) U.S. Cl.
CPC ........ *A61M 5/3204* (2013.01); *A61M 5/3202* (2013.01); *A61M 5/3213* (2013.01); *A61M 5/3219* (2013.01); *A61M 5/3257* (2013.01)

(58) Field of Classification Search
CPC .............. A61M 5/3204; A61M 5/3202; A61M 5/3213; A61M 5/3219; A61M 5/3257
See application file for complete search history.

(56) References Cited

U.S. PATENT DOCUMENTS

| | | | |
|---|---|---|---|
| 8,591,463 | B1 | 11/2013 | Cowe |
| 8,708,968 | B2 | 4/2014 | Julian |
| 2008/0228147 | A1 | 9/2008 | David-Hegerich et al. |
| 2010/0160869 | A1 | 6/2010 | Liversidge |
| 2010/0286619 | A1* | 11/2010 | Abry ................... A61M 5/2033 604/192 |
| 2012/0130342 | A1 | 5/2012 | Cleathero |
| 2012/0191047 | A1 | 7/2012 | Raday et al. |

(Continued)

FOREIGN PATENT DOCUMENTS

| | | |
|---|---|---|
| AU | 2012209222 | 5/2013 |
| CN | 101264360 | 9/2008 |

(Continued)

OTHER PUBLICATIONS

European Search Report in European Application No. 14162455.1, dated Aug. 7, 2014, 7 pages.

(Continued)

*Primary Examiner* — Dung T Ulsh
(74) *Attorney, Agent, or Firm* — Fish & Richardson P.C.

(57) ABSTRACT

The disclosure relates to a sheath removal mechanism (15) for removing a protective needle sheath (5) from a medicament container (3), the medicament container (3) arrangeable in an medicament delivery device (1), wherein the sheath removal mechanism (15) comprises a cap (11) attachable to a distal end of the medicament delivery device (1), wherein the cap (11) comprises at least one ledge (11.6) adapted to engage a protective needle sheath (5).

19 Claims, 20 Drawing Sheets

(56) References Cited

U.S. PATENT DOCUMENTS

| | | | |
|---|---|---|---|
| 2012/0203186 A1 | 8/2012 | Vogt et al. | |
| 2014/0243753 A1* | 8/2014 | Bostrom | A61M 5/3219 604/198 |
| 2014/0343503 A1* | 11/2014 | Holmqvist | A61M 5/3202 604/192 |
| 2015/0051553 A1 | 2/2015 | Bjork | |
| 2015/0174325 A1* | 6/2015 | Young | A61M 5/2033 604/135 |
| 2015/0174337 A1 | 6/2015 | Takemoto | |
| 2015/0272778 A1* | 10/2015 | Clarke | A61M 5/3202 604/192 |
| 2016/0015905 A1* | 1/2016 | Fournier | A61M 5/3202 604/192 |
| 2016/0106929 A1* | 4/2016 | Fournier | A61M 5/3202 604/192 |
| 2016/0144132 A1* | 5/2016 | Scanlon | A61M 5/3204 604/192 |
| 2016/0243315 A1* | 8/2016 | Perche | A61M 5/3204 |
| 2016/0271338 A1 | 9/2016 | Fournier | |
| 2016/0325044 A1 | 11/2016 | Tschirren | |
| 2016/0367763 A1 | 12/2016 | Tschirren | |
| 2017/0014578 A1 | 1/2017 | Bunch | |
| 2017/0173269 A1 | 6/2017 | Wozencroft | |
| 2017/0274152 A1 | 9/2017 | Bostrom | |

FOREIGN PATENT DOCUMENTS

| | | |
|---|---|---|
| CN | 101454037 | 6/2009 |
| CN | 101489610 | 7/2009 |
| CN | 101827622 | 9/2010 |
| CN | 101854967 | 10/2010 |
| CN | 101868270 | 10/2010 |
| CN | 102065934 | 5/2011 |
| EP | 2364740 | 9/2011 |
| EP | 2468340 | 6/2012 |
| GB | 2414400 | 11/2005 |
| GB | 2438593 | 12/2007 |
| JP | WO 2005/115508 | 12/2005 |
| JP | 2008-500855 | 1/2008 |
| JP | 2009-538661 | 11/2009 |
| JP | 2010-540054 | 12/2010 |
| JP | 2010-540055 | 12/2010 |
| JP | 2013-521083 | 6/2013 |
| JP | 2014-500089 | 1/2014 |
| JP | 2014-503279 | 2/2014 |
| JP | 2014-526297 | 10/2014 |
| JP | 2016-508807 | 3/2016 |
| WO | WO 2007/138296 | 12/2007 |
| WO | WO 2007/138299 | 12/2007 |
| WO | WO 2009/019439 | 2/2009 |
| WO | WO 2009/040601 | 4/2009 |
| WO | WO 2009/040603 | 4/2009 |
| WO | WO 2009/040607 | 4/2009 |
| WO | WO 2009/153544 | 12/2009 |
| WO | WO 2011/110465 | 9/2011 |
| WO | WO 2012/073032 | 6/2012 |
| WO | WO 2012/085031 | 6/2012 |
| WO | WO 2012/122643 | 9/2012 |
| WO | WO 2013/006119 | 1/2013 |
| WO | WO 2013/034984 | 3/2013 |

OTHER PUBLICATIONS

International Preliminary Report on Patentability in International Application No. PCT/EP2015/056687, dated Oct. 4, 2016, 7 pages.
International Search Report and Written Opinion in International Application No. PCT/EP2015/056687, dated Jun. 22, 2015, 11 pages.
Wikipedia.org [online], "Snap-fit," Aug. 9, 2017, retrieved on Feb. 12, 2018, retrieved from URL <https://en.wikipedia.org/wiki/Snap-fit>, 3 pages.

* cited by examiner

SHEATH REMOVAL MECHANISM

CROSS-REFERENCE TO RELATED APPLICATIONS

This application is a continuation of U.S. application Ser. No. 15/124,790, filed Sep. 9, 2016, which is a U.S. national stage application under 35 USC § 371 of International Application No. PCT/EP2015/056687, filed on Mar. 27, 2015, which claims priority to European Patent Application No. 14162455.1, filed on Mar. 28, 2014, the entire contents of which are incorporated herein by reference.

TECHNICAL FIELD

The disclosure relates to a sheath removal mechanism for removing a needle sheath from a needle in a medicament delivery device.

BACKGROUND OF THE DISCLOSURE

Administering an injection is a process which presents a number of risks and challenges for users and healthcare professionals, both mental and physical. Medicament delivery devices typically fall into two categories—manual devices and autoinjectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the medicament delivery device, administering the injection and keeping the medicament delivery device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Usually the injection needle is equipped with a protective needle sheath for keeping the needle sterile and preventing it from being mechanically damaged. The protective needle sheath is attached to the needle when the auto-injector or the medicament container is assembled. In order to prepare for an injection, the protective needle sheath must be removed, which may expose a user to a high risk of needle stick injuries.

There remains a need for an improved sheath removal mechanism.

SUMMARY OF THE DISCLOSURE

Certain aspects of the subject matter described in the present disclosure to provide an improved sheath removal mechanism.

The aspect is implemented by a sheath removal mechanism according to claim 1.

Exemplary embodiments of the disclosure are given in the dependent claims.

According to the disclosure, a sheath removal mechanism is provided for removing a protective needle sheath from a medicament container, the medicament container arrangeable in a medicament delivery device, wherein the sheath removal mechanism comprises a cap attachable to a distal end of the medicament delivery device, wherein the cap comprises at least one ledge adapted to engage a protective needle sheath.

In an exemplary embodiment, the ledge is respectively arranged on at least one sheath removal beam arranged on the cap.

In an exemplary embodiment, the sheath removal beam extends in a proximal direction from a distal face of the cap or is part of an interval sleeve extending in the proximal direction from a distal face of the cap.

In an exemplary embodiment, the sheath removal beam is compliant.

In an exemplary embodiment, the ledge is compliant.

In an exemplary embodiment, the sheath removal mechanism further comprises an internal casework arranged on a case of the medicament delivery device, the casework adapted to radially outwardly support the sheath removal beam to prevent its radial outward deflection during movement of the cap away from the case.

In an exemplary embodiment, the sheath removal mechanism further comprises a portion of a needle shroud, the portion adapted to radially outwardly support the sheath removal beam to prevent its radial outward deflection during movement of the cap away from the case.

In an exemplary embodiment, the portion or the casework is adapted to allow radial outward deflection of the sheath removal beam during insertion of a medicament container with a protective needle sheath into the case.

In an exemplary embodiment, the ledge is adapted to engage proximally behind a proximal end of the protective needle sheath or into a lateral recess within the protective needle sheath.

In an exemplary embodiment, the sheath removal mechanism further comprises a ramp on the sheath removal beam for engaging the protective needle sheath in a manner to radially outwardly deflect the sheath removal beam during insertion of the protective needle sheath.

In an exemplary embodiment, the sheath removal beam and/or a proximal face of the portion or the casework are/is ramped for radially inwardly deflecting the sheath removal beam during removal of the cap from the case.

In an exemplary embodiment, the ledges provide a clearance between them sufficiently wide to allow a protective needle sheath to pass through when the compliant sheath removal beams are in a relaxed state, wherein one or more snap fits are arranged on the compliant sheath removal beams in a manner to engage a neighbouring compliant sheath removal beam when the sheath removal beams are radially inwardly deflected.

In an exemplary embodiment, the needle shroud is adapted to deflect the compliant sheath removal beams radially inwards when being moved in the proximal direction.

In an exemplary embodiment, one or more holes or lateral apertures or openings are arranged in the distal face or in a lateral area of the cap to allow insertion of at least one assembling tool.

In an exemplary embodiment, a wedge shaped assembly tool is provided, adapted to be inserted through the lateral aperture or through the opening and to engage between two of the sheath removal beams for splaying them apart thereby deflecting them in a radial outward direction and increasing the clearance defined by the inward ledges to an extent allowing a protective needle sheath to pass through.

In an exemplary embodiment, a cap for a medicament container has a protective needle sheath removably disposed on a needle, the cap comprising:
- a distal face;
- at least one compliant sheath removal beam extending in a proximal direction from the distal face and defining a space for receiving a protective needle sheath, the at least one compliant sheath removal beam including at least one ledge adapted to engage the protective needle sheath,
- wherein the at least one compliant sheath removal beam is disposed approximately perpendicular to the distal face in a first position for engaging the protective needle sheath and is disposed at a non-approximately perpendicular angle to the distal face in a second position for receiving the protective needle sheath.

In an exemplary embodiment, the ledge is compliant.

In an exemplary embodiment of the at least one compliant sheath removal beam is biased toward the first position.

In another exemplary embodiment, the at least one compliant sheath removal beam is biased toward the second position.

In an exemplary embodiment, the at least one compliant sheath removal beam radially abuts a needle shroud or an internal casework to maintain the at least one compliant sheath removal beam in the first position.

In an exemplary embodiment, the ledge is adapted to engage proximally behind a proximal end of the protective needle sheath or into a recess within the protective needle sheath.

In an exemplary embodiment, the at least one compliant sheath removal beam includes a proximally-disposed ramp adapted to abut the protective needle sheath.

In an exemplary embodiment, the at least one compliant sheath removal beam includes one or more snap fits adapted to engage one or more corresponding snap fits on a neighbouring compliant sheath removal beam when the at least one compliant sheath removal beam and the neighbouring compliant sheath removal beam are in the first position.

In an exemplary embodiment, the cap further comprises one or more holes or lateral apertures are arranged in the distal face or in a lateral area of the cap to allow insertion of at least one assembling tool for applying a force to move the at least one compliant sheath removal beam from the first position to the second position.

In an exemplary embodiment, the at least one sheath removal beam is moulded in the first position.

The sheath removal mechanism according to the disclosure allows for engaging the protective needle sheath during assembly. When the cap is removed from the case of the medicament delivery device in preparation of an injection the sheath removal mechanism pulls out the protective needle sheath reliably without exposing the user to too high a risk to injure themselves. The sheath removal mechanism is suited for removing a protective needle sheath even if the protective needle sheath is arranged far behind an orifice of the medicament delivery device making it impossible to be gripped manually. Thus the needle can be arranged in the case initially a distance back from the orifice in order to prevent the user from touching the tip of the needle after the protective needle sheath is removed.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
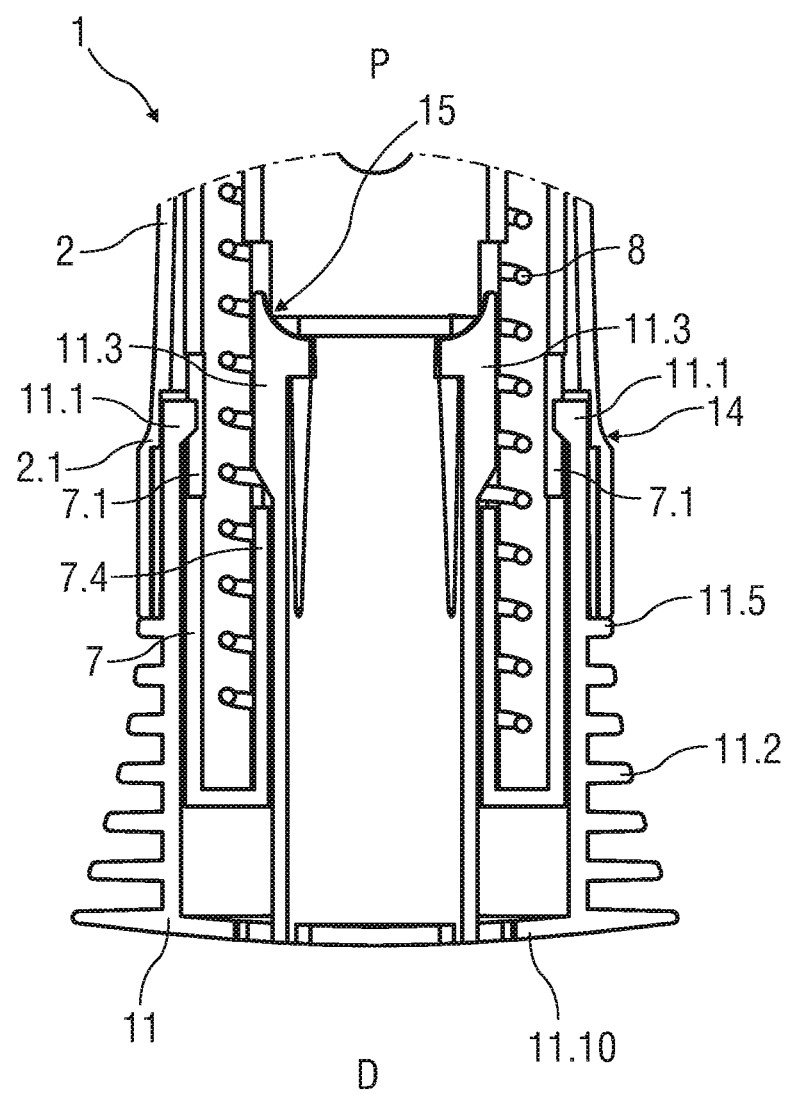
FIG. 1 is a schematic view of a distal end of an exemplary embodiment of a medicament delivery device according to the present disclosure during assembly.

FIG. 1 is a schematic view of a distal end of an exemplary first embodiment of a medicament delivery device 1 according to the present disclosure during assembly. The medicament delivery device 1 comprises a case 2 adapted to hold a medicament container, such as a medicament container, ampoule, cartridge, etc., having a needle fixed or removably coupled thereto.

In an exemplary embodiment, a cap 11 may be removably disposed at a distal end of the case 2. The cap 11 may include an element (e.g., a barb, a hook, a narrowed section, etc.) arranged to engage the case 2, a needle shroud 7 telescoped within the case, and/or a protective needle sheath on the needle. The protective needle sheath may be rubber and/or plastic. In an exemplary embodiment, the protective needle sheath is a rigid needle shield (RNS) formed from a rubber interior adapted to engage the needle with a plastic exterior at least partially covering an outer portion of the rubber interior. The cap 11 may comprise grip features 11.2 for facilitating removal of the cap 11 (e.g., by twisting and/or pulling the cap 11 relative to the case 2). In an exemplary embodiment, the grip features 11.2 may include one or more ribs, ridges, projections, bumps, notches, textured surfaces, or an overmolded coating (rubber, elastic, etc.), etc.

In an exemplary embodiment, a shroud spring 8 is arranged to bias the needle shroud 7 distally toward an extended position relative to the case 2. During use, the device 1 is pressed against an injection site causing the needle shroud 7 to move proximally relative to the case 2 to a retracted position against the biasing force of the shroud spring 8.

In an exemplary embodiment, a first shroud lock mechanism 14 is arranged to prevent retraction of the needle shroud 7 relative to the case 2 when the cap 11 is in place, thereby avoiding unintentional activation of the medicament delivery device 1 (e.g., if dropped, during shipping or packaging, etc.). The first shroud lock mechanism 14 may comprise one or more male elements (e.g., compliant interlock beams 11.1) on the cap 11 and a respective number of female elements (e.g., apertures 7.1 or recesses) in the needle shroud 7 adapted to receive each of the male elements. In another exemplary embodiment, male elements may be disposed on the needle shroud 7, and the female elements may be disposed on the cap 11.

In an exemplary embodiment, a sheath removal mechanism 15 is arranged engage the protective needle sheath and remove it from the needle as the cap 11 is removed from the medicament delivery device 1. The sheath removal mechanism 15 may comprise one or more compliant sheath removal beams 11.3 on the cap 11 adapted to engage the protective needle sheath. Typically, the sheath removal beams 11.3 extend in a proximal direction P from a distal face 11.10 of the cap 11 or are part of an internal sleeve extending in the proximal direction P from a distal face 11.10 of the cap 11.

In an exemplary embodiment, the cap 11 is assembled to the medicament delivery device 1 by being moved in a proximal direction P relative to the needle shroud 7. When the cap 11 is being attached to the medicament delivery device 1, the compliant interlock beams 11.1 are deflected radially outward around the needle shroud 7, relax into the apertures 7.1 within the needle shroud 7 and abut a radial stop 2.1 on the case 2 which prevents the compliant interlock beams 11.1 from disengaging the apertures 7.1. When the cap 11 is being attached to the medicament delivery device 1, the sheath removal beams 11.3 are deflected radially inwards for entering the needle shroud 7. When the cap 11 is fully attached to the medicament delivery device 1, the sheath removal beams 11.3 are no longer radially restricted by the needle shroud 7 thus allowing radial outward deflection of the sheath removal beams 11.3 around the protective needle sheath.

When the cap 11 is attached to the medicament delivery device 1, axial movement of the cap 11 in the proximal direction P relative the case 2 may be limited by a rib 11.5 on the cap 11 abutting the case 2.

Figure 2:
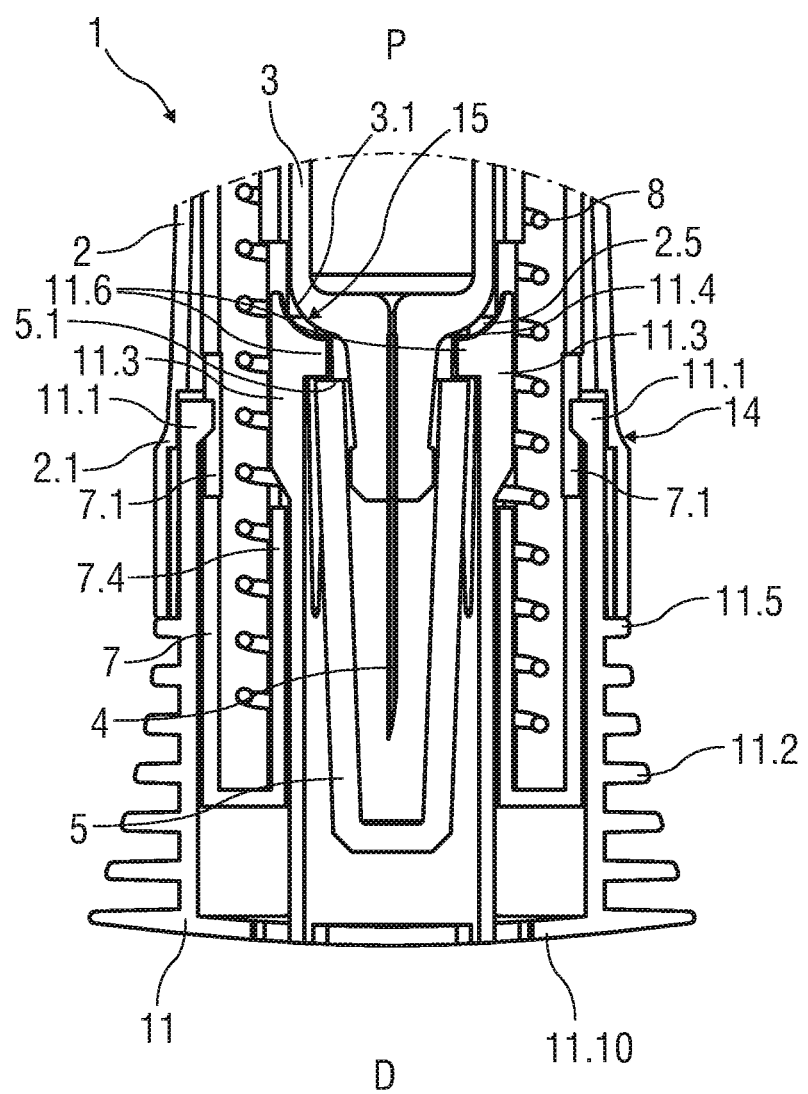
FIG. 2 is a schematic view of the distal end of the medicament delivery device with the assembled cap during assembly of a medicament container with a protective needle sheath.

FIG. 2 is a schematic view of the distal end of the medicament delivery device 1 with the assembled cap 11 during assembly of a medicament container 3 with a protective needle sheath 5. The medicament container 3 may be a pre-filled medicament container and have a needle 4 arranged at a distal end. When the medicament delivery device 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container may be a cartridge which includes the medicament M and engages a removable needle (e.g., by threads, snaps, friction, etc.).

The medicament container 3 and the protective needle sheath 5 are inserted into the case 2 and pushed in the distal direction D. During the insertion, the protective needle sheath 5 abuts ramps 11.4 on the sheath removal beams 11.3 and deflects them radially outward thus allowing insertion of the protective needle sheath 5 between the sheath removal beams 11.3. Upon further movement in the distal direction D the protective needle sheath 5 passes inward ledges 11.6 on the sheath removal beams 11.3. Thus, the sheath removal beams 11.3 relax radially inwards and the inward ledges 11.6 engage a proximal end 5.1 of the protective needle sheath 5 thus axially coupling the cap 11 to the protective needle sheath 5. In an exemplary embodiment the case 2 (or another component, such as for example, a syringe carrier) may comprise an axial stop 2.5 limiting axial movement of the medicament container 3 within the case 2 in the distal direction D, e.g. by engaging a neck portion 3.1 of the medicament container 3.

Figure 3:
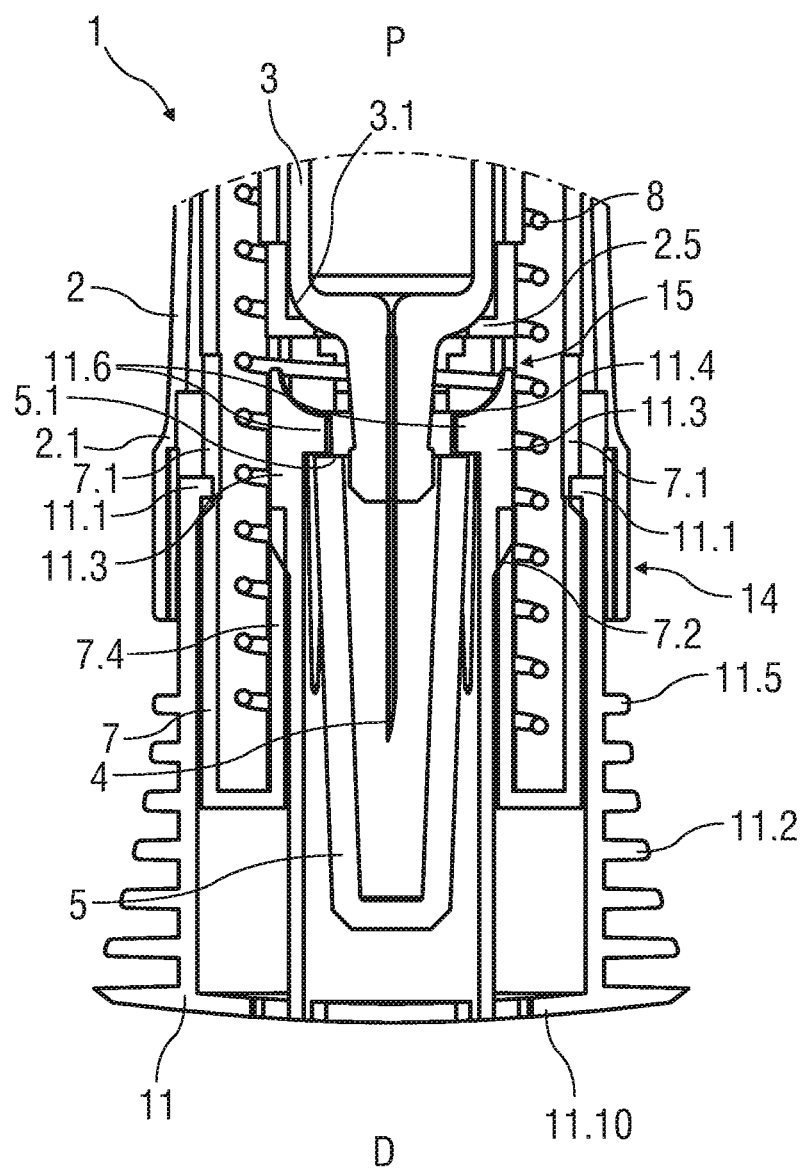
FIG. 3 is a schematic view of the distal end of the medicament delivery device during removal of the cap.

FIG. 3 is a schematic view of the distal end of the medicament delivery device 1 during removal of the cap 11.

When the cap 11 is pulled in the distal direction D relative to the case 2, the compliant interlock beams 11.1 are axially removed from the radial stops 2.1 allowing outward deflection of the compliant interlock beams 11.1. On further movement of the cap 11 in the distal direction D, the compliant interlock beams 11.1 may abut an edge of the aperture 7.1 and deflect to disengage the aperture 7.1, allowing for removal of the cap 11 and the protective needle sheath 5 attached thereto by the inward ledges 11.6 of the sheath removal beams 11.3. In an exemplary embodiment, the compliant interlock beams 11.1 and/or the apertures 7.1 may be ramped to reduce force necessary to disengage the compliant interlock beams 11.1 from the apertures 7.1. In an exemplary embodiment the sheath removal beams 11.3 and/or a proximal face 7.2 of the portion 7.4 of the needle shroud 7 adapted to radially outwardly support the sheath removal beams 11.3 may be ramped to further push the sheath removal beams 11.3 radially inward onto the protective needle sheath 5 to prevent the sheath removal beams 11.3 from disengaging the protective needle sheath 5 during cap removal.

Figure 4:
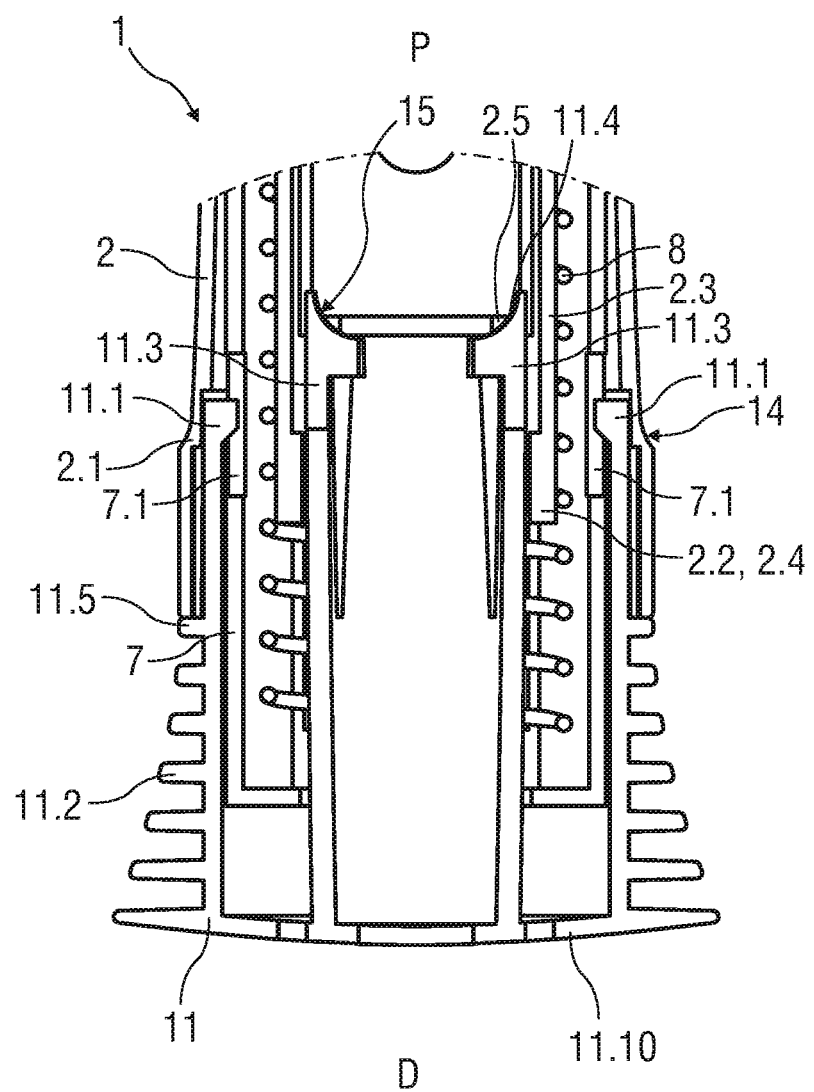
FIG. 4 is a schematic view of a distal end of an exemplary second embodiment of a medicament delivery device according to the present disclosure during assembly.

FIG. 4 is a schematic view of a distal end of an exemplary second embodiment of a medicament delivery device 1 according to the present disclosure during assembly. The medicament delivery device 1 comprises a case 2 adapted to hold a medicament container.

In an exemplary embodiment, a cap 11 may be removably disposed at a distal end of the case 2. The cap 11 may include an element (e.g., a barb, a hook, a narrowed section, etc.) arranged to engage the case 2, a needle shroud 7 telescoped within the case, and/or a protective needle sheath on the needle. The protective needle sheath may be rubber and/or plastic. In an exemplary embodiment, the protective needle sheath is a rigid needle shield (RNS) formed from a rubber interior adapted to engage the needle with a plastic exterior at least partially covering an outer portion of the rubber interior. The cap 11 may comprise grip features 11.2 for facilitating removal of the cap 11 (e.g., by twisting and/or pulling the cap 11 relative to the case 2). In an exemplary embodiment, the grip features 11.2 may include one or more ribs, ridges, projections, bumps, notches, textured surfaces, or an overmolded coating (rubber, elastic, etc.), etc.

In an exemplary embodiment, a shroud spring 8 is arranged to bias the needle shroud 7 distally toward an extended position relative to the case 2. During use, the device 1 is pressed against an injection site causing the needle shroud 7 to move proximally relative to the case 2 to a retracted position against the biasing force of the shroud spring 8.

In an exemplary embodiment, a sheath removal mechanism 15 is arranged engage the protective needle sheath and remove it from the needle as the cap 11 is removed from the medicament delivery device 1. The sheath removal mechanism 15 may comprise one or more compliant sheath removal beams 11.3 on the cap 11 adapted to engage the protective needle sheath. Typically, the sheath removal beams 11.3 extend in a proximal direction P from a distal face 11.10 of the cap 11 or are part of an internal sleeve extending in the proximal direction P from a distal face 11.10 of the cap 11.

The cap 11 is assembled to the medicament delivery device 1 by being moved in a proximal direction P relative to the needle shroud 7. When the cap 11 is being attached to the medicament delivery device 1, the compliant interlock beams 11.1 are deflected around the needle shroud 7, relax into the apertures 7.1 within the needle shroud 7 and abut a radial stop 2.1 on the case 2 which prevents the compliant interlock beams 11.1 from disengaging the apertures 7.1. When the cap 11 is being attached to the medicament delivery device 1, the sheath removal beams 11.3 are inserted through internal casework 2.2 attached to the case 2. The casework 2.2 provides sufficient clearance to allow this.

When the cap 11 is attached to the medicament delivery device 1, axial movement of the cap 11 in the proximal direction P relative the case 2 is limited by a rib 11.5 on the cap 11 abutting the case 2.

Figure 5:
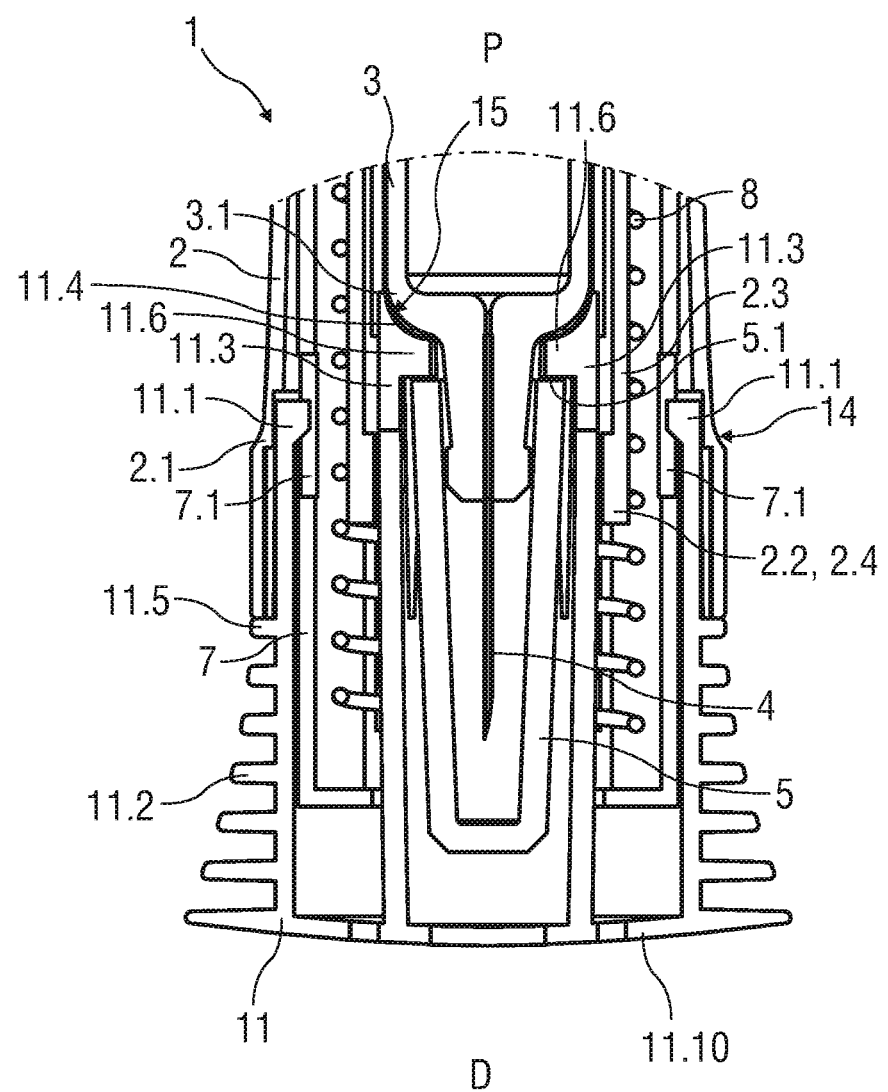
FIG. 5 is a schematic view of the distal end of the medicament delivery device with an assembled cap during assembly of a medicament container with a protective needle sheath.

FIG. 5 is a schematic view of the distal end of the medicament delivery device 1 with the assembled cap 11 during assembly of a medicament container 3 with a protective needle sheath 5. The medicament container 3 may be a pre-filled medicament container and have a needle 4 arranged at a distal end. When the medicament delivery device 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container may be a cartridge which includes the medicament M and engages a removable needle (e.g., by threads, snaps, friction, etc.).

The medicament container 3 and the protective needle sheath 5 are inserted into the case 2 and pushed in the distal direction D. During the insertion, the protective needle sheath 5 abuts ramps 11.4 on the sheath removal beams 11.3 and deflects them radially outward thus allowing insertion of the protective needle sheath 5 between the sheath removal beams 11.3. Radial outward deflection of the sheath removal beams 11.3 is facilitated by a wide section 2.3 within the casework 2.2. Upon further movement in the distal direction D the protective needle sheath 5 passes inward ledges 11.6 on the sheath removal beams 11.3. Thus, the sheath removal beams 11.3 relax radially inwards and the inward ledges 11.6 engage a proximal end 5.1 of the protective needle sheath 5 thus axially coupling the cap 11 to the protective needle sheath 5. In an exemplary embodiment the case 2 may comprise an axial stop 2.5 limiting axial movement of the medicament container 3 within the case 2 in the distal direction D, e.g. by engaging a neck portion 3.1 of the medicament container 3.

Figure 6:
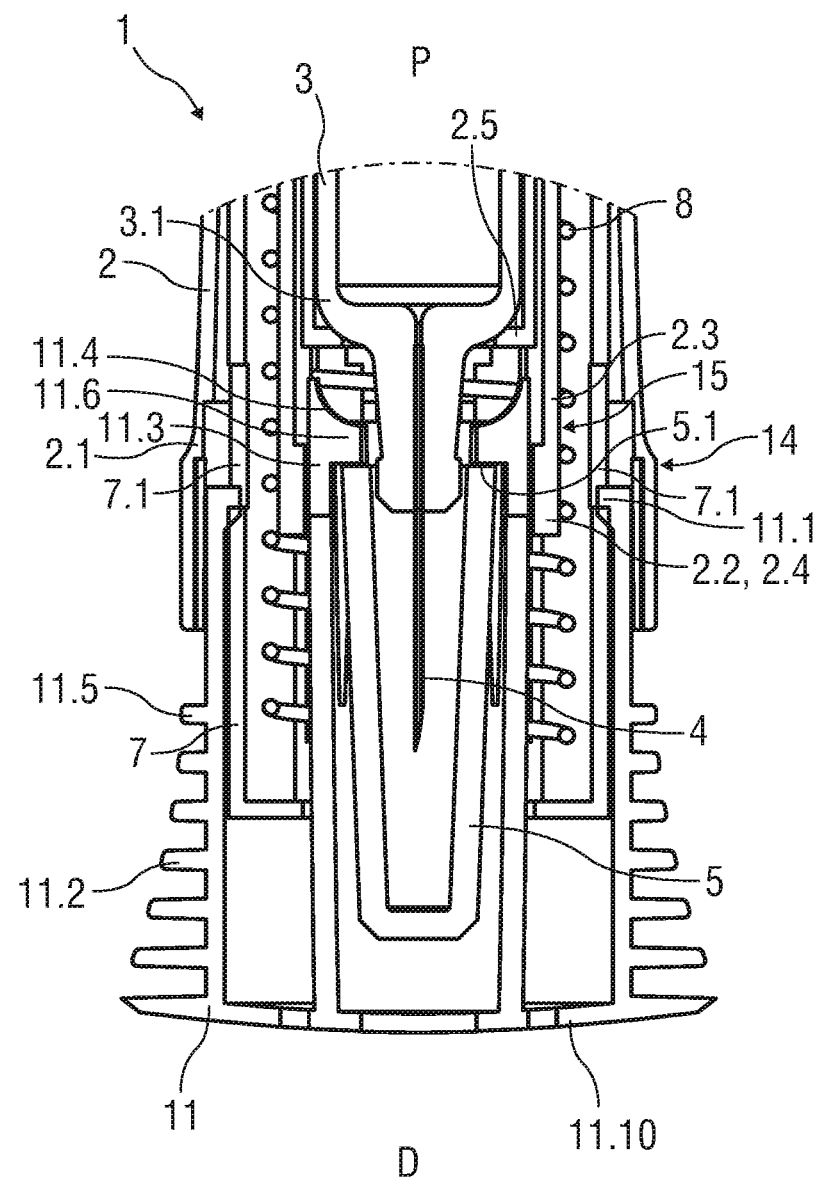
FIG. 6 is a schematic view of the distal end of the medicament delivery device during removal of the cap.

FIG. 6 is a schematic view of the distal end of the medicament delivery device 1 during removal of the cap 11.

When the cap 11 is pulled in the distal direction D relative to the case 2, the compliant interlock beams 11.1 are axially removed from the radial stops 2.1 allowing outward deflection of the compliant interlock beams 11.1. On further movement of the cap 11 in the distal direction D, the compliant interlock beams 11.1 may abut an edge of the aperture 7.1 and deflect to disengage the aperture 7.1, allowing for removal of the cap 11 and the protective needle sheath 5 attached thereto by the inward ledges 11.6 of the sheath removal beams 11.3. In an exemplary embodiment, the compliant interlock beams 11.1 and/or the apertures 7.1 may be ramped to reduce force necessary to disengage the compliant interlock beams 11.1 from the apertures 7.1. In an exemplary embodiment the wide section 2.3 of the casework 2.2 is distally followed by a narrow section 2.4 with a reduced diameter as opposed to the wide section 2.3 to prevent the sheath removal beams 11.3 from disengaging the protective needle sheath 5 during cap removal.

Figure 7A:
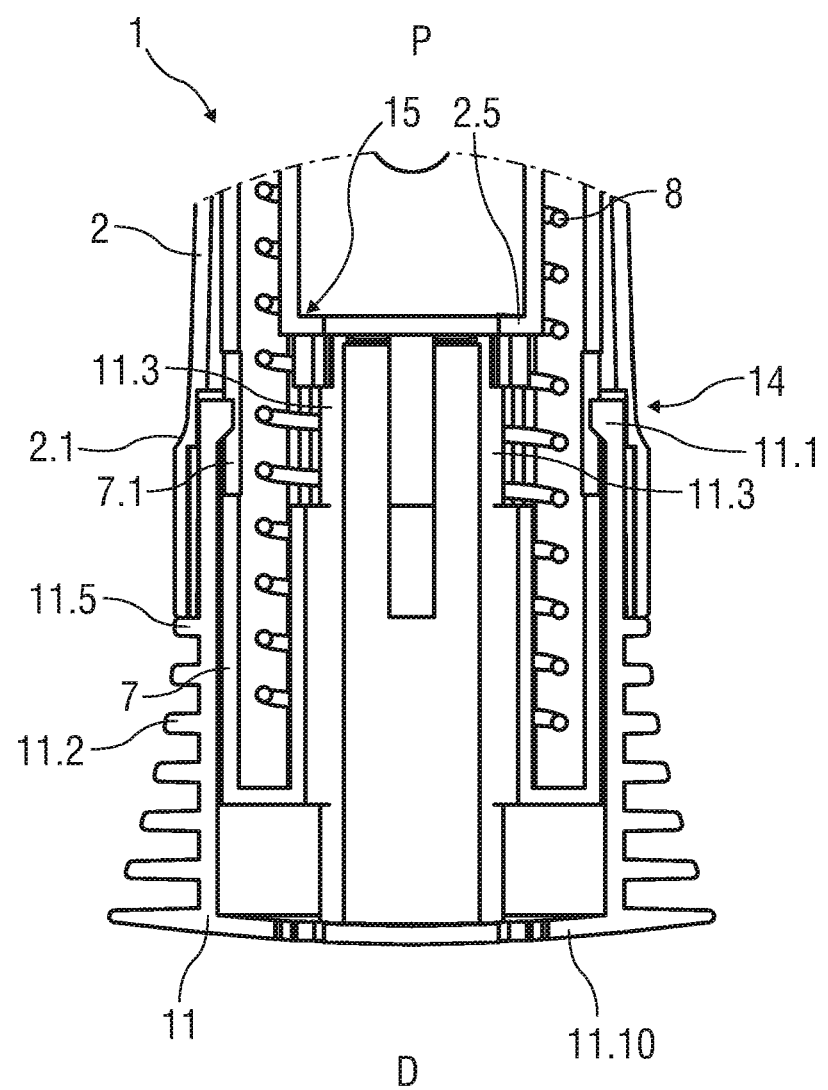
FIG. 7A is a schematic view of a distal end of an exemplary third embodiment of a medicament delivery device according to the present disclosure during assembly.

FIG. 7A is a schematic view of a distal end of an exemplary third embodiment of an medicament delivery device 1 according to the present disclosure during assembly. The medicament delivery device 1 comprises a case 2 adapted to hold a medicament container, such as a medicament container.

In an exemplary embodiment, a cap 11 may be removably disposed at a distal end of the case 2. The cap 11 may include an element (e.g., a barb, a hook, a narrowed section, etc.) arranged to engage the case 2, a needle shroud 7 telescoped within the case, and/or a protective needle sheath on the needle. The protective needle sheath may be rubber and/or plastic. In an exemplary embodiment, the protective needle sheath is a rigid needle shield (RNS) formed from a rubber interior adapted to engage the needle with a plastic exterior at least partially covering an outer portion of the rubber interior. The cap 11 may comprise grip features 11.2 for facilitating removal of the cap 11 (e.g., by twisting and/or pulling the cap 11 relative to the case 2). In an exemplary embodiment, the grip features 11.2 may include one or more ribs, ridges, projections, bumps, notches, textured surfaces, or an overmolded coating (rubber, elastic, etc.), etc.

In an exemplary embodiment, a shroud spring 8 is arranged to bias the needle shroud 7 distally toward an extended position relative to the case 2. During use, the device 1 is pressed against an injection site causing the needle shroud 7 to move proximally relative to the case 2 to a retracted position against the biasing force of the shroud spring 8.

In an exemplary embodiment, a first shroud lock mechanism 14 is arranged to prevent retraction of the needle shroud 7 relative to the case 2 when the cap 11 is in place, thereby avoiding unintentional activation of the medicament delivery device 1 (e.g., if dropped, during shipping or packaging, etc.). The first shroud lock mechanism 14 may comprise one or more male elements (e.g., compliant interlock beams 11.1) on the cap 11 and a respective number of female elements (e.g., apertures 7.1 or recesses) in the needle shroud 7 adapted to receive each of the male elements. In another exemplary embodiment, male elements may be disposed on the needle shroud 7, and the female elements may be disposed on the cap 11. In a further exemplary embodiment, the male elements may be disposed on the cap 11, and the female elements may be disposed on the case 2, or vice-versa.

Figure 7B:
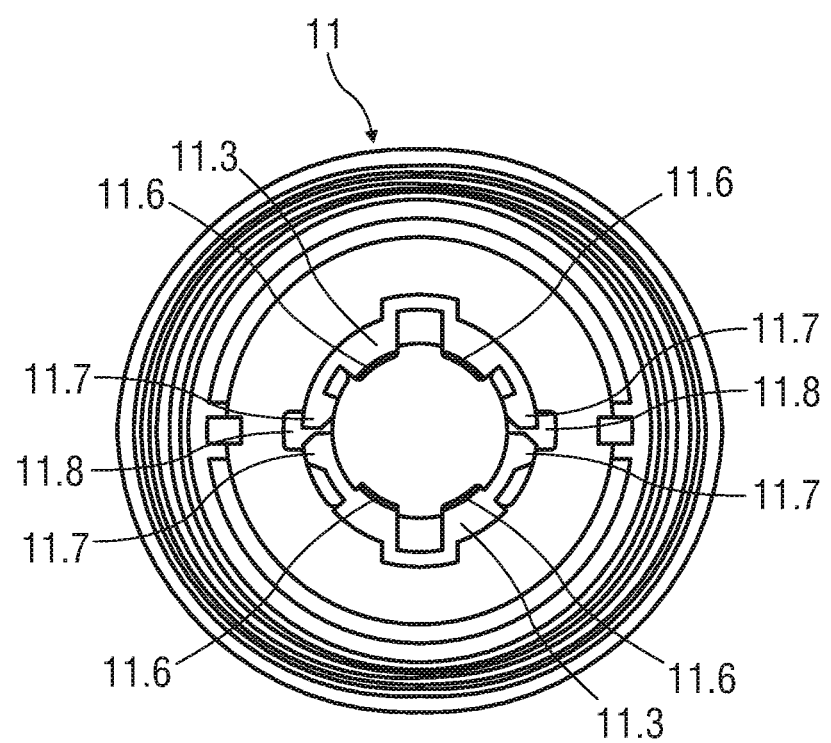
FIG. 7B is a schematic view of a cap of the medicament delivery device during assembly.

In an exemplary embodiment, a sheath removal mechanism 15 is arranged to remove the protective needle sheath from the medicament container on removal of the cap 11 from the medicament delivery device 1. The sheath removal mechanism 15 may comprise one or more compliant sheath removal beams 11.3 on the cap 11 adapted to engage the protective needle sheath. Typically, the sheath removal beams 11.3 extend in a proximal direction P from a distal face 11.10 of the cap 11 or are part of an internal sleeve extending in the proximal direction P from a distal face 11.10 of the cap 11. As shown in FIG. 7B the compliant sheath removal beams 11.3 comprise respective inward ledges 11.6. When the compliant sheath removal beams 11.3 are relaxed as in FIG. 7B the ledges 11.6 provide a clearance between them sufficiently wide to allow a protective needle sheath to pass through. One or more snap fits 11.7 are arranged on the compliant sheath removal beams 11.3 in a manner to engage neighbouring compliant sheath removal beams 11.3 once they are radially inwardly deflected. One or more holes 11.8 may be arranged in a distal face 11.10 of the cap 11 to allow insertion of assembling tools.

Referring again to FIG. 7A the cap 11 is assembled to the medicament delivery device 1 by being moved in a proximal direction P relative to the needle shroud 7. When the cap 11 is being attached to the medicament delivery device 1, the compliant interlock beams 11.1 are deflected around the needle shroud 7, relax into the apertures 7.1 within the needle shroud 7 and abut a radial stop 2.1 on the case 2 which prevents the compliant interlock beams 11.1 from disengaging the apertures 7.1. When the cap 11 is being attached to the medicament delivery device 1, the sheath removal beams 11.3 are inserted into the needle shroud 7 which is sufficiently wide to allow this.

When the cap 11 is attached to the medicament delivery device 1, axial movement of the cap 11 in the proximal direction P relative the case 2 is limited by a rib 11.5 on the cap 11 abutting the case 2.

Figure 8:
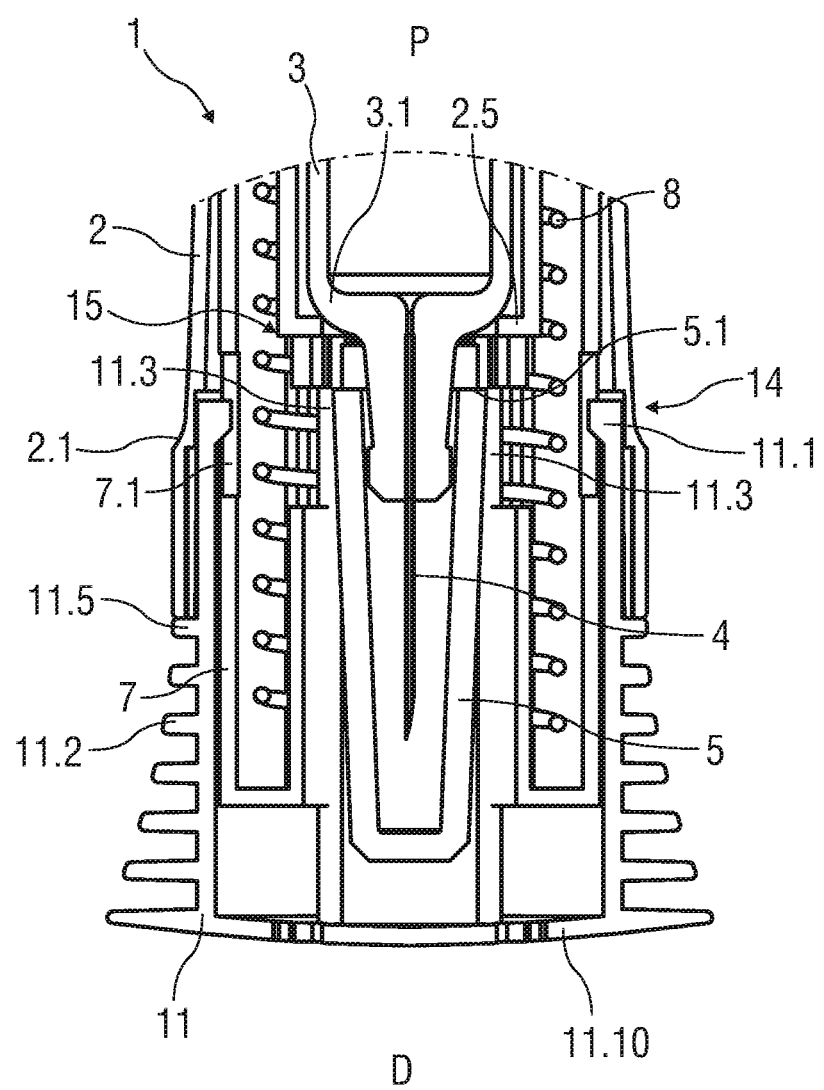
FIG. 8 is a schematic view of the distal end of the medicament delivery device with the assembled cap during assembly of a medicament container with a protective needle sheath.

FIG. 8 is a schematic view of the distal end of the medicament delivery device 1 with the assembled cap 11 during assembly of a medicament container 3 with a protective needle sheath 5. The medicament container 3 may be a pre-filled medicament container and have a needle 4 arranged at a distal end. When the medicament delivery device 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container may be a cartridge which includes the medicament M and engages a removable needle (e.g., by threads, snaps, friction, etc.).

The medicament container 3 and the protective needle sheath 5 are inserted into the case 2 and pushed in the distal direction D. The clearance between the ledges 11.6 on the compliant sheath removal beams 11.3 is wide enough to receive the protective needle sheath 5. In an exemplary embodiment the case 2 may comprise an axial stop 2.5 limiting axial movement of the medicament container 3 within the case 2 in the distal direction D, e.g. by engaging a neck portion 3.1 of the medicament container 3.

Figure 9A:
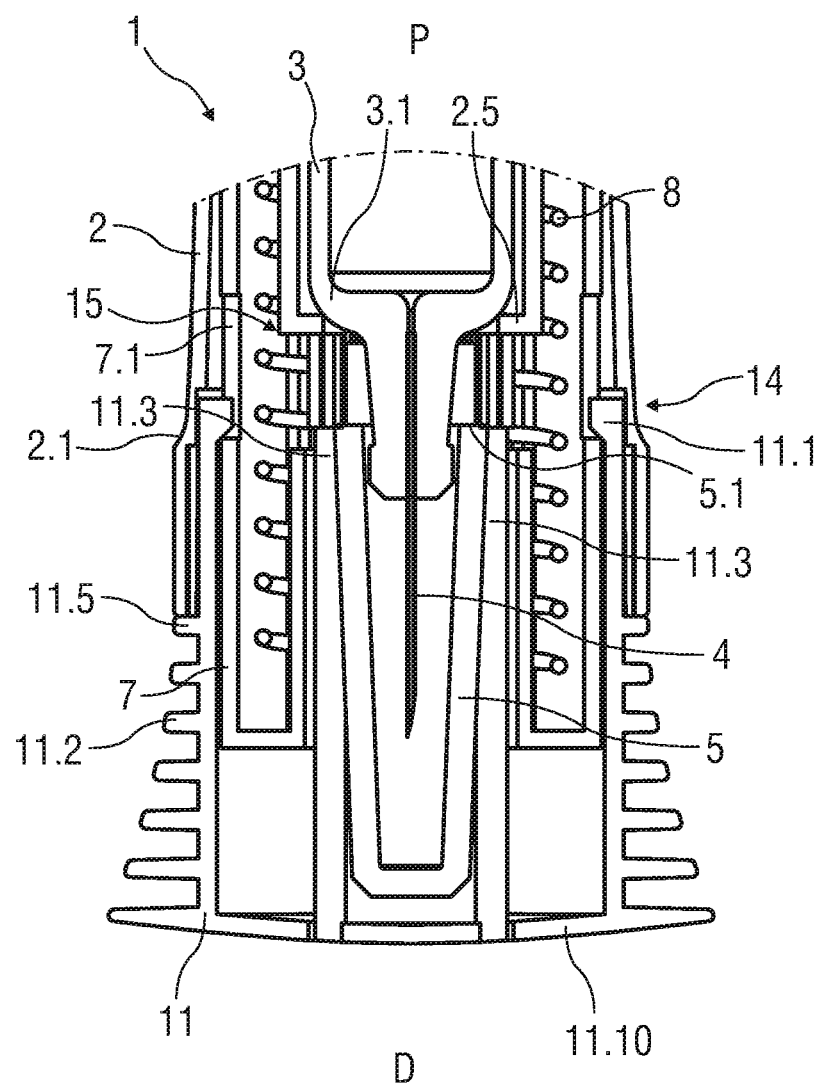
FIG. 9A is a schematic view of the distal end of the medicament delivery device with the assembled cap, medicament container and protective needle sheath.
Figure 9B:
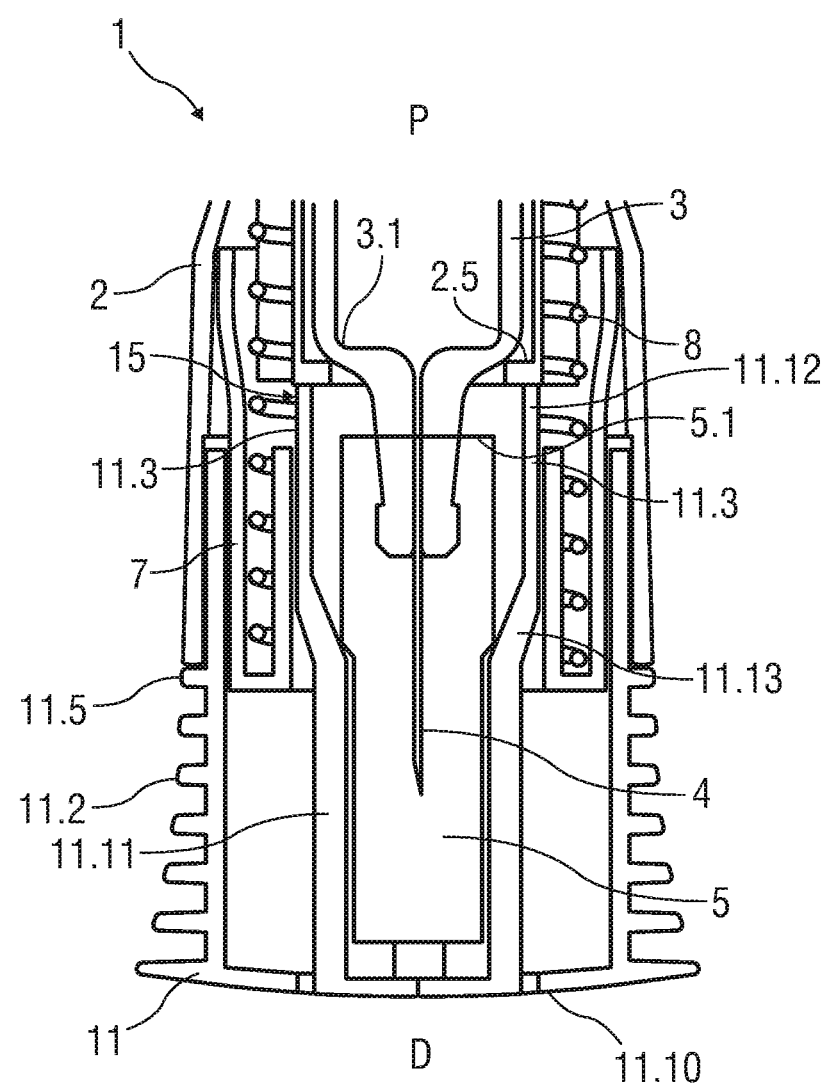
FIG. 9B is a schematic view of the distal end of the medicament delivery device with the assembled cap, medicament container and protective needle sheath.

FIGS. 9A and 9B are schematic longitudinal section of the distal end of the medicament delivery device 1 with the assembled cap 11, medicament container 3 and protective needle sheath 5 in different section planes. FIG. 9B illustrates that the compliant sheath removal beams 11.3 respectively comprise a distal portion 11.11 defining an internal sleeve with a diameter smaller than an internal diameter of the needle shroud 7 so that the distal portions 11.11 do not interfere with the needle shroud 7. Respective proximal portions 11.12 of the sheath removal beams 11.3 define a diameter of the internal sleeve greater than the internal diameter of the needle shroud 7. The distal portion 11.11 and the proximal portion 11.12 are connected by a tapered portion 11.13. In order to allow assembly of the cap 11 to the medicament delivery device 1 the sheath removal beams 11.3 may be radially inwardly deflected such that the diameter of the internal sleeve defined by the proximal portions 11.12 is reduced for allowing passing through the internal diameter of the needle shroud 7. For this purpose the snap fits 11.7 may be engaged for assembly of the cap 11 and disengaged once the cap 11 is in place, e.g. by a tool (not illustrated) inserted through the holes 11.8, allowing the sheath removal beams 11.3 to relax radially outwards for permitting insertion of the protective needle sheath 5. In this state the needle shroud 7 is still in the position shown in FIG. 8, not interfering with the sheath removal beams 11.3.

Figure 9C:
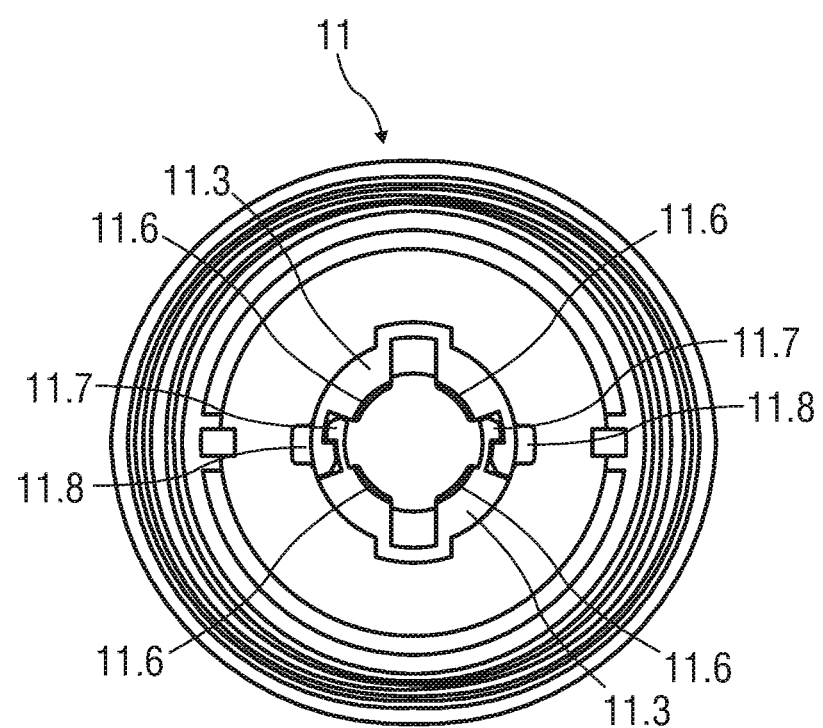
FIG. 9C is a schematic view of the cap of the medicament delivery device during assembly.

In FIG. 9B the needle shroud 7 has been depressed in the proximal direction P by a defined distance. This may be achieved by a tool (not illustrated) inserted through the holes 11.8. As the needle shroud 7 moves it engages the tapered portions 11.13 and then the proximal portions 11.12 of the sheath removal beams 11.3 deflecting the compliant sheath removal beams 11.3 radially inwards until their snap-fits 11.7 engage as best seen in FIG. 9C. Hence, the inward ledges 11.6 reduce the clearance between them and engage a proximal end 5.1 of the protective needle sheath 5 thus axially coupling the cap 11 to the protective needle sheath 5.

Figure 10:
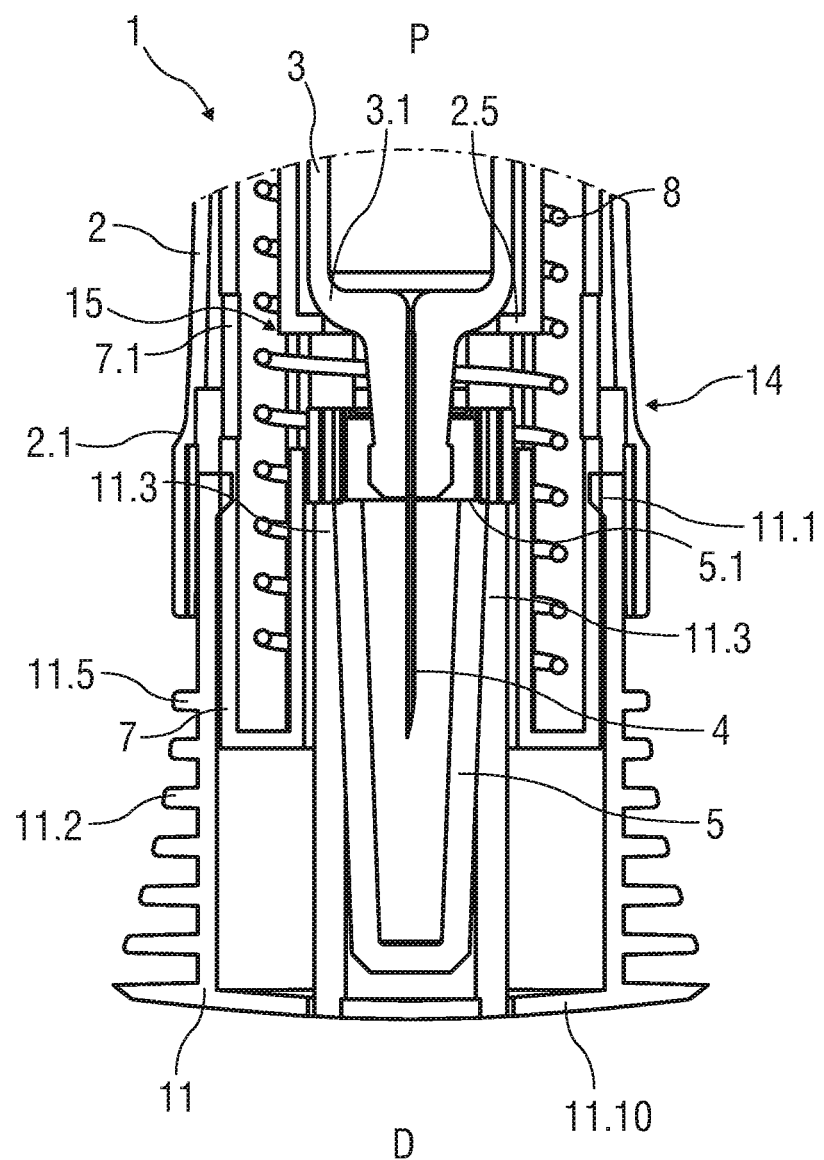
FIG. 10 is a schematic view of the distal end of the medicament delivery device during removal of the cap.

FIG. 10 is a schematic view of the distal end of the medicament delivery device 1 during removal of the cap 11.

When the cap 11 is pulled in the distal direction D relative to the case 2, the compliant interlock beams 11.1 are axially removed from the radial stops 2.1 allowing outward deflection of the compliant interlock beams 11.1. On further movement of the cap 11 in the distal direction D, the compliant interlock beams 11.1 may abut an edge of the aperture 7.1 and deflect to disengage the aperture 7.1, allowing for removal of the cap 11 and the protective needle sheath 5 attached thereto by the sheath removal beams 11.3.

In an exemplary embodiment, the compliant interlock beams 11.1 and/or the apertures 7.1 may be ramped to reduce force necessary to disengage the compliant interlock beams 11.1 from the apertures 7.1.

As the sheath removal beams 11.3 are snap fitted to each other the ledges 11.6 remain engaged to the proximal end of the protective needle sheath 5 throughout the cap removal thus removing the protective needle sheath 5 from the medicament container 3.

Figure 11:
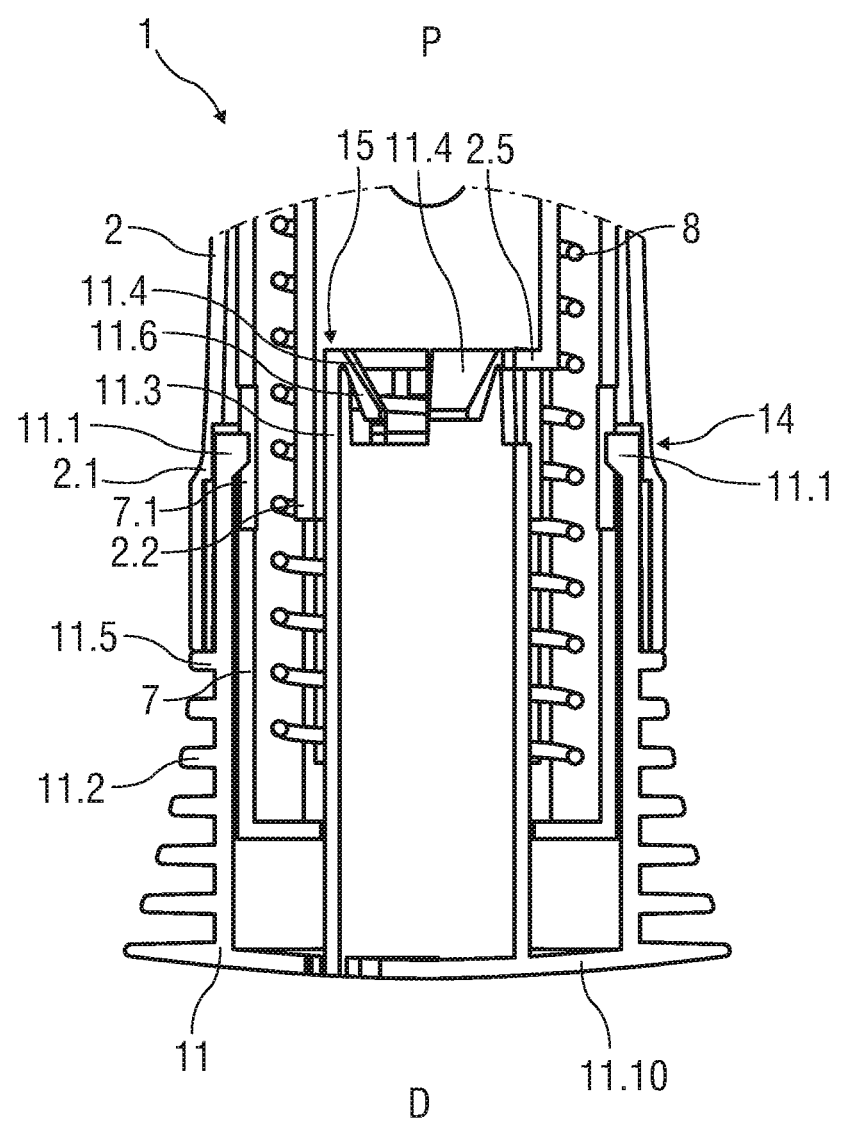
FIG. 11 is a schematic view of a distal end of an exemplary fourth embodiment of a medicament delivery device according to the present disclosure during assembly.

FIG. 11 is a schematic view of a distal end of an exemplary fourth embodiment of a medicament delivery device 1 according to the present disclosure during assembly. The medicament delivery device 1 comprises a case 2 adapted to hold a medicament container, such as a medicament container.

In an exemplary embodiment, a cap 11 may be removably disposed at a distal end of the case 2. The cap 11 may include an element (e.g., a barb, a hook, a narrowed section, etc.) arranged to engage the case 2, a needle shroud 7 telescoped within the case, and/or a protective needle sheath on the needle. The protective needle sheath may be rubber and/or plastic. In an exemplary embodiment, the protective needle sheath is a rigid needle shield (RNS) formed from a rubber interior adapted to engage the needle with a plastic exterior at least partially covering an outer portion of the rubber interior. The cap 11 may comprise grip features 11.2 for facilitating removal of the cap 11 (e.g., by twisting and/or pulling the cap 11 relative to the case 2). In an exemplary embodiment, the grip features 11.2 may include one or more ribs, ridges, projections, bumps, notches, textured surfaces, or an overmolded coating (rubber, elastic, etc.), etc.

In an exemplary embodiment, a shroud spring 8 is arranged to bias the needle shroud 7 distally toward an extended position relative to the case 2. During use, the device 1 is pressed against an injection site causing the needle shroud 7 to move proximally relative to the case 2 to a retracted position against the biasing force of the shroud spring 8.

In an exemplary embodiment, a first shroud lock mechanism 14 is arranged to prevent retraction of the needle shroud 7 relative to the case 2 when the cap 11 is in place, thereby avoiding unintentional activation of the medicament delivery device 1 (e.g., if dropped, during shipping or packaging, etc.). The first shroud lock mechanism 14 may comprise one or more male elements (e.g., compliant interlock beams 11.1) on the cap 11 and a respective number of female elements (e.g., apertures 7.1 or recesses) in the needle shroud 7 adapted to receive each of the male elements. In another exemplary embodiment, male elements may be disposed on the needle shroud 7, and the female elements may be disposed on the cap 11. In a further exemplary embodiment, the male elements may be disposed on the cap 11, and the female elements may be disposed on the case 2, or vice-versa.

In an exemplary embodiment, a sheath removal mechanism 15 is arranged to remove the protective needle sheath from the medicament container on removal of the cap 11 from the medicament delivery device 1. The sheath removal mechanism 15 may comprise one or more sheath removal beams 11.3 on the cap 11 adapted to engage the protective needle sheath. Typically, the sheath removal beams 11.3 extend in a proximal direction P from a distal face 11.10 of the cap 11 or are part of an internal sleeve extending in the proximal direction P from a distal face 11.10 of the cap 11. The sheath removal beams 11.3 comprise respective compliant inward ledges 11.6 which when relaxed define a clearance between them smaller than a diameter of a protective needle sheath to be inserted.

The cap 11 is assembled to the medicament delivery device 1 by being moved in a proximal direction P relative to the needle shroud 7. When the cap 11 is being attached to the medicament delivery device 1, the compliant interlock beams 11.1 are deflected around the needle shroud 7, relax into the apertures 7.1 within the needle shroud 7 and abut a radial stop 2.1 on the case 2 which prevents the compliant interlock beams 11.1 from disengaging the apertures 7.1. When the cap 11 is being attached to the medicament delivery device 1, the sheath removal beams 11.3 are inserted into the needle shroud 7 and through internal casework 2.2 attached to the case 2. The casework 2.2 provides sufficient clearance to allow this but radially outwardly supports the sheath removal beams 11.3 preventing them from being radially outwardly deflected.

When the cap 11 is attached to the medicament delivery device 1, axial movement of the cap 11 in the proximal direction P relative the case 2 is limited by a rib 11.5 on the cap 11 abutting the case 2.

Figure 12:
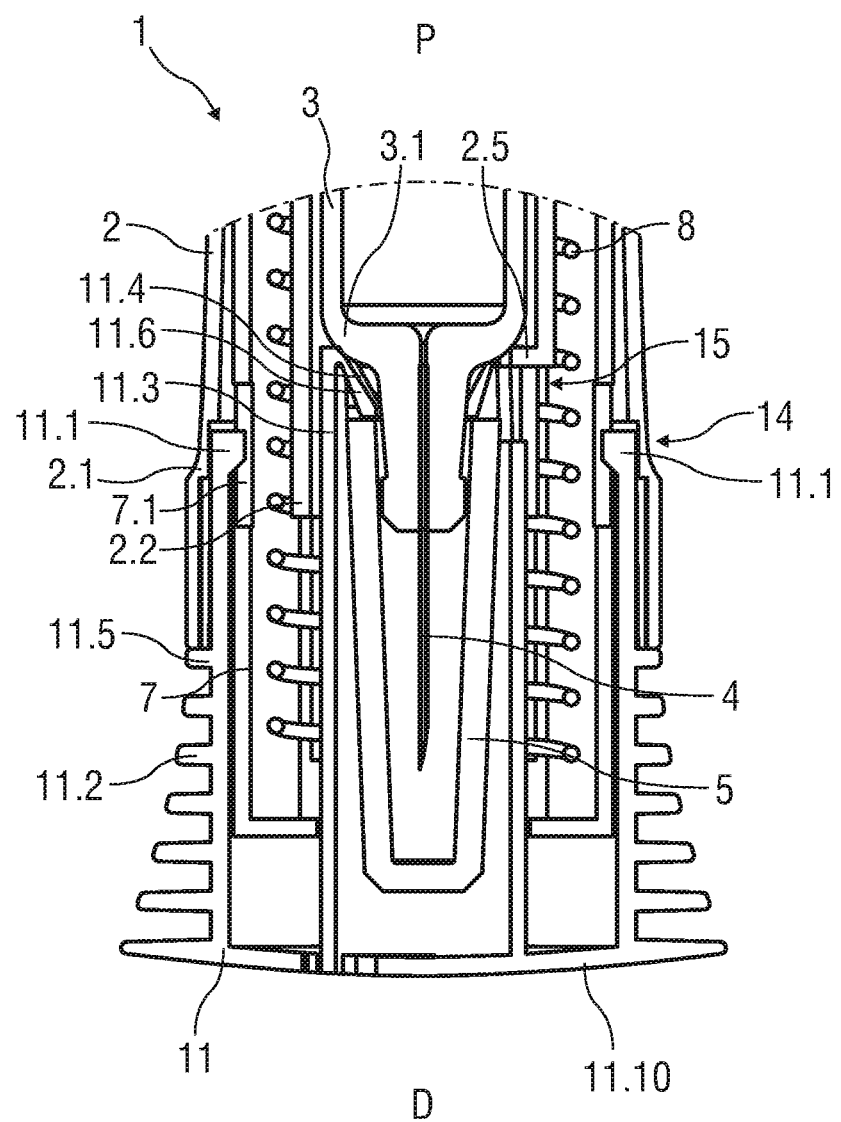
FIG. 12 is a schematic view of the distal end of the medicament delivery device with the assembled cap during assembly of a medicament container with a protective needle sheath.

FIG. 12 is a schematic view of the distal end of the medicament delivery device 1 with the assembled cap 11 during assembly of a medicament container 3 with a protective needle sheath 5. The medicament container 3 may be a pre-filled medicament container and have a needle 4 arranged at a distal end. When the medicament delivery device 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container may be a cartridge which includes the medicament M and engages a removable needle (e.g., by threads, snaps, friction, etc.).

The medicament container 3 and the protective needle sheath 5 are inserted into the case 2 and pushed in the distal direction D. During the insertion, the protective needle sheath 5 abuts ramps 11.4 on the ledges 11.6 and deflects the ledges 11.6 radially outward thus allowing insertion of the protective needle sheath 5 between the sheath removal beams 11.3. Upon further movement in the distal direction D the protective needle sheath 5 passes the ledges 11.6 allowing them to relax radially outwards. The ledges 11.6 engage a proximal end 5.1 of the protective needle sheath 5 thus axially coupling the cap 11 to the protective needle sheath 5. In an exemplary embodiment the case 2 may comprise an axial stop 2.5 limiting axial movement of the medicament container 3 within the case 2 in the distal direction D, e.g. by engaging a neck portion 3.1 of the medicament container 3.

When the cap 11 is pulled in the distal direction D relative to the case 2, the compliant interlock beams 11.1 are axially removed from the radial stops 2.1 allowing outward deflection of the compliant interlock beams 11.1. On further movement of the cap 11 in the distal direction D, the compliant interlock beams 11.1 may abut an edge of the aperture 7.1 and deflect to disengage the aperture 7.1, allowing for removal of the cap 11 and the protective needle sheath 5 attached thereto by the sheath removal beams 11.3. In an exemplary embodiment, the compliant interlock beams 11.1 and/or the apertures 7.1 may be ramped to reduce force necessary to disengage the compliant interlock beams 11.1 from the apertures 7.1.

When the cap 11 is pulled in the distal direction D relative to the case 2, the inward ledges 11.6 engage the proximal end 5.1 of the protective needle sheath 5 and pull it in the distal direction D away from the medicament container 3. The casework 2.2 outwardly supports the sheath removal beams 11.3 preventing them from radially outwardly deflecting and from disengaging the protective needle sheath 5. The casework 2.2 extends sufficiently far in the distal direction D to provide this support until the friction between the protective needle sheath 5 and the medicament container 3 during removal ceases.

Figure 13A:
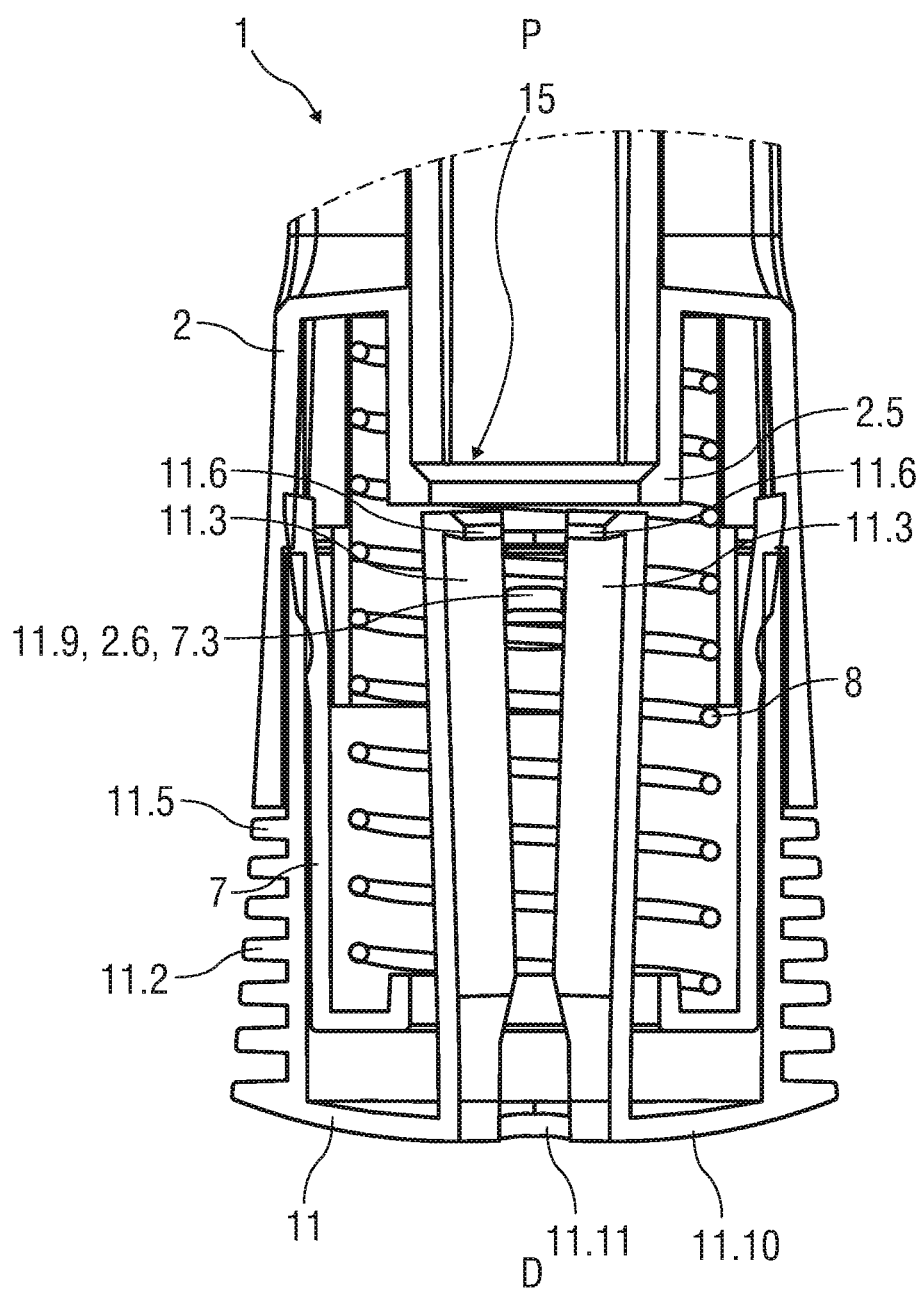
FIG. 13A is a schematic view of a distal end of an exemplary fifth embodiment of a medicament delivery device according to the present disclosure during assembly.

FIG. 13A is a schematic view of a distal end of an exemplary fifth embodiment of a medicament delivery device 1 according to the present disclosure during assembly. The medicament delivery device 1 comprises a case 2 adapted to hold a medicament container, such as a syringe.

In an exemplary embodiment, a cap 11 may be removably disposed at a distal end of the case 2. The cap 11 may include an element (e.g., a barb, a hook, a narrowed section, etc.) arranged to engage the case 2, a needle shroud 7 telescoped within the case, and/or a protective needle sheath on the needle. The protective needle sheath may be rubber and/or plastic. In an exemplary embodiment, the protective needle sheath is a rigid needle shield (RNS) formed from a rubber interior adapted to engage the needle with a plastic exterior at least partially covering an outer portion of the rubber interior. The cap 11 may comprise grip features 11.2 for facilitating removal of the cap 11 (e.g., by twisting and/or pulling the cap 11 relative to the case 2). In an exemplary embodiment, the grip features 11.2 may include one or more ribs, ridges, projections, bumps, notches, textured surfaces, or an overmolded coating (rubber, elastic, etc.), etc.

In an exemplary embodiment, a shroud spring 8 is arranged to bias the needle shroud 7 distally toward an extended position relative to the case 2. During use, the device 1 is pressed against an injection site causing the needle shroud 7 to move proximally relative to the case 2 to a retracted position against the biasing force of the shroud spring 8.

Figure 13B:
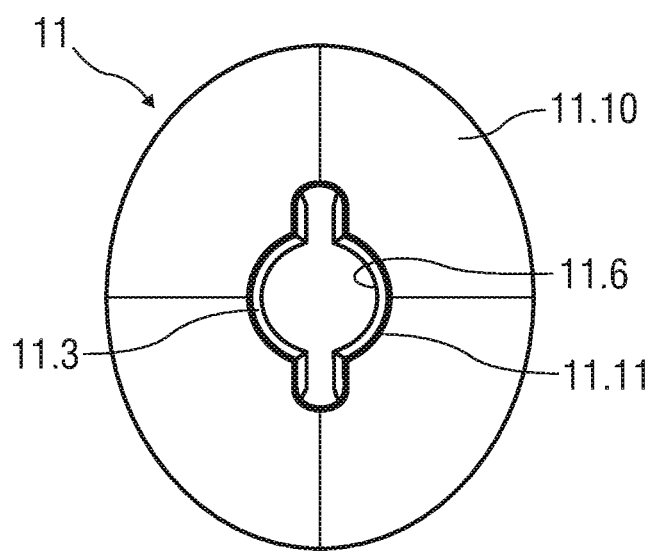
FIG. 13B is a schematic view of an exemplary embodiment of a cap to be attached to a medicament delivery device.

In an exemplary embodiment, a sheath removal mechanism 15 is arranged to remove the protective needle sheath from the medicament container on removal of the cap 11 from the medicament delivery device 1. The sheath removal mechanism 15 may comprise one or more compliant sheath removal beams 11.3 on the cap 11 adapted to engage the protective needle sheath. Typically, the sheath removal beams 11.3 extend in a proximal direction P from a distal face 11.10 of the cap 11 or are part of an internal sleeve extending in the proximal direction P from a distal face 11.10 of the cap 11. The compliant sheath removal beams 11.3 comprise respective inward ledges 11.6. When the compliant sheath removal beams 11.3 are relaxed the ledges 11.6 provide a clearance between them smaller than a diameter of a protective needle sheath. In an exemplary embodiment, one or more assembly tools may be inserted in an axial direction through portion(s) of an opening 11.11 in the distal face 11.10 of the cap 11. FIG. 13B is a schematic view of an exemplary embodiment of the cap 11. The opening 11.11 may be shaped similar to a keyhole such that an assembly tool may be inserted therethrough and engage the sheath removal beams 11.7, causing the sheath removal beams 11.7 to deflect to receive a protective needle sheath.

In another exemplary embodiment one or more lateral apertures 11.9 are arranged in a lateral area of the cap 11 to allow insertion of an assembling tool. Corresponding lateral apertures 2.6, 7.3 may likewise be arranged in the case 2 and the needle shroud 7 in such a manner that a set of lateral apertures 11.9, 2.6, 7.3 respectively aligns when the cap 11 is attached to the case 2.

The cap 11 is assembled to the medicament delivery device 1 by being moved in a proximal direction P relative to the needle shroud 7. When the cap 11 is being attached to the medicament delivery device 1, the sheath removal beams 11.3 are inserted into the needle shroud 7 which is sufficiently wide to allow this.

When the cap 11 is attached to the medicament delivery device 1, axial movement of the cap 11 in the proximal direction P relative the case 2 is limited by a rib 11.5 on the cap 11 abutting the case 2.

Figure 14:
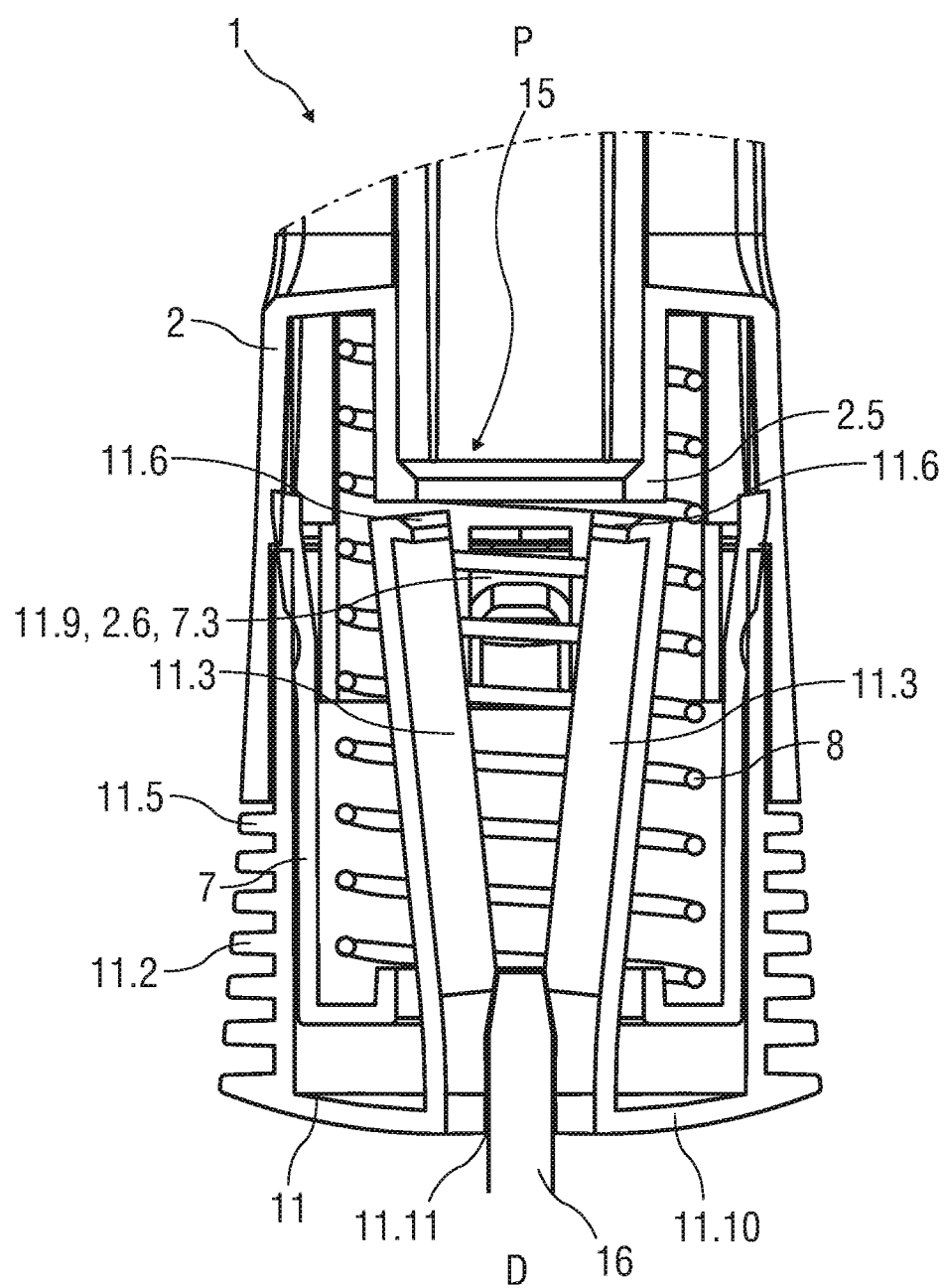
FIG. 14 is a schematic view of the distal end of the medicament delivery device with the assembled cap during insertion of a wedge shaped assembly tool through an aligned set of lateral apertures.

FIG. 14 is a schematic view of the distal end of the medicament delivery device 1 with the assembled cap 11 during insertion of a wedge shaped assembly tool 16 through the opening 11.11 in the distal face 11.10. The wedge shaped assembly tool 16 engages between two of the sheath removal beams 11.3 splaying them apart thereby deflecting them in a radial outward direction. This opens up the clearance defined by the inward ledges 11.6 to an extent allowing a protective needle sheath to pass through. In an exemplary embodiment the wedge shaped assembly tool 16 can also be arranged to displace the shroud 7 axially in the same motion enabling the engagement of the second shroud lock mechanism 15 and priming of the plunger release mechanism 12.

Figure 15:
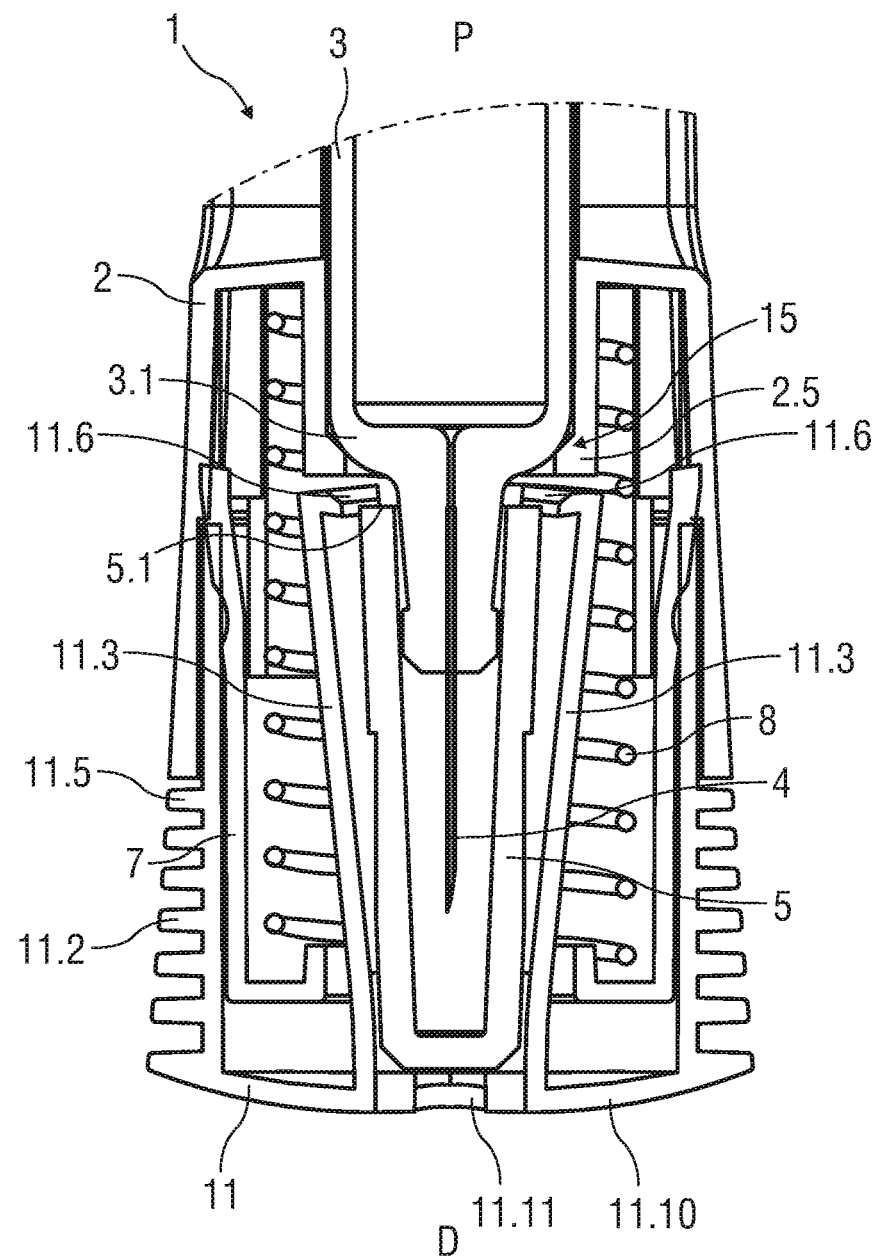
FIG. 15 is a schematic view of the distal end of the medicament delivery device with the assembled cap and the inserted assembly tool during assembly of a medicament container with a protective needle sheath.

FIG. 15 is a schematic view of the distal end of the medicament delivery device 1 with the assembled cap 11 during assembly of a medicament container 3 with a protective needle sheath 5. The medicament container 3 may be a pre-filled medicament container and have a needle 4 arranged at a distal end. When the medicament delivery device 1 and/or the medicament container 3 are assembled, a protective needle sheath 5 may be removably coupled to the needle 4. The protective needle sheath 5 may be a rubber needle sheath or a rigid needle sheath (which is composed of rubber and a full or partial plastic shell). In other exemplary embodiments, the medicament container may be a cartridge which includes the medicament M and engages a removable needle (e.g., by threads, snaps, friction, etc.).

The medicament container 3 and the protective needle sheath 5 are inserted into the case 2 and pushed in the distal direction D. Due to the assembly tool 16 the clearance between the ledges 11.6 on the compliant sheath removal beams 11.3 is wide enough to allow insertion of the protective needle sheath 5. In an exemplary embodiment the case 2 may comprise an axial stop 2.5 limiting axial movement of the medicament container 3 within the case 2 in the distal direction D, e.g. by engaging a neck portion 3.1 of the medicament container 3.

Figure 16:
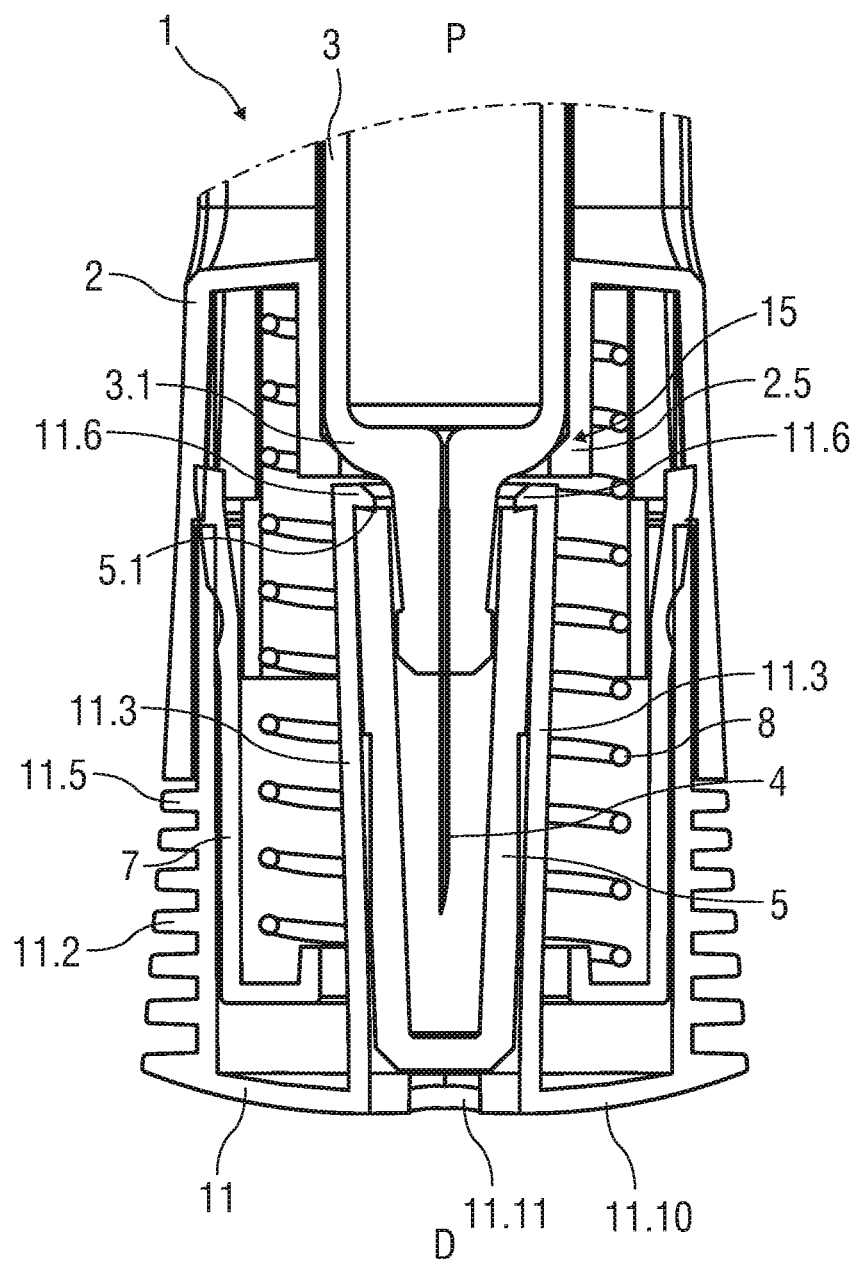
FIG. 16 is a schematic view of the distal end of the medicament delivery device with the assembled cap, medicament container and protective needle sheath.

FIG. 16 is a schematic view of the distal end of the medicament delivery device 1 with the assembled cap 11, medicament container 3 and protective needle sheath 5. The assembly tool 16 is removed from the opening 11.11 in the distal face 11.10 of the cap 11 such that the sheath removal beams 11.3 are no longer splayed apart. Due to their beam stiffness the sheath removal beams 11.3 relax radially inwards, the inward ledges 11.6 reduce the clearance between them and engage a proximal end 5.1 of the protective needle sheath 5 thus axially coupling the cap 11 to the protective needle sheath 5. In an exemplary embodiment the sheath removal beams 11.3 are moulded in an inward deflected position which ensures they are always in intimate contact with the protective needle sheath 5 once the tool is removed. The wedge shaped assembly tool 16 is designed so that the sheath removal beams 11.3 are not deformed so far as to plastically yield. The contact point between the protective needle sheath 5 and the sheath removal beams 11.3 is arranged to minimise the moment acting to open the sheath removal beams 11.3 as the protective needle sheath 5 is removed. Hence, gripping of the protective needle sheath 5 does not rely on radial compressive force exerted by the sheath removal beams 11.3 but on a force exerted to the cap 11 in the distal direction D relative to the case 2. In an exemplary embodiment of the wedge shaped assembly tool 16 may be arranged to splay the sheath removal beams 11.3 in a direction perpendicular to the direction of the force exerted to the cap 11 during cap removal.

When the cap 11 is pulled in the distal direction D relative to the case 2, the ledges 11.6 engaged to the proximal end 5.1 of the protective needle sheath 5 pull the protective needle sheath 5 off the medicament container 3.

Those of skill in the art will understand that the embodiment of FIGS. 13 to 16 may be provided with the first shroud lock mechanism 14 of the other embodiments.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

The invention claimed is:

1. A sheath removal mechanism for removing a protective needle sheath from a medicament container that is arrangeable in a medicament delivery device, the sheath removal mechanism comprising:
   an assembly tool; and
   a cap attachable to a distal end of the medicament delivery device,
   wherein the cap comprises a plurality of sheath removal beams and a plurality of inward ledges respectively arranged on the plurality of sheath removal beams and adapted to engage the protective needle sheath,
   wherein the cap defines one or more openings arranged on a distal-most face of the cap and configured to allow insertion of the assembly tool, and
   wherein the cap defines an outer surface configured to be touched by a user for removing the cap from the distal end of the medicament delivery device.

2. The sheath removal mechanism according to claim 1, wherein the assembly tool is configured to be inserted through the one or more openings and to engage between two sheath removal beams of the plurality of sheath removal beams for splaying the two sheath removal beams apart, thereby deflecting the two sheath removal beams in a radially outward direction and increasing a clearance defined respectively by two inward ledges of the plurality of inward ledges to allow the protective needle sheath to pass therethrough.

3. The sheath removal mechanism according to claim 2, wherein the sheath removal mechanism is configured such that when the assembly tool is disposed within the cap, a needle of the medicament delivery device is shielded from the assembly tool by the protective needle sheath.

4. The sheath removal mechanism according to claim 2, wherein the assembly tool is further configured to axially displace a shroud of the medicament delivery device.

5. The sheath removal mechanism according to claim 2, wherein the assembly tool comprises a wedge-shaped end portion that is complimentary to a distal portion of the cap.

6. The sheath removal mechanism according to claim 1, wherein the plurality of sheath removal beams extends in a proximal direction from the distal-most face of the cap or is part of an internal sleeve extending in the proximal direction from the distal-most face of the cap.

7. The sheath removal mechanism according to claim 1, wherein the plurality of sheath removal beams is compliant.

8. The sheath removal mechanism according to claim 1, wherein the plurality of inward ledges is compliant.

9. The sheath removal mechanism according to claim 1, further comprising an internal casework arranged on a case of the medicament delivery device, the internal casework adapted to radially outwardly support the plurality of sheath removal beams to prevent radially outward deflection of the plurality of sheath removal beams during movement of the cap away from the case.

10. The sheath removal mechanism according to claim 9, wherein the internal casework is adapted to allow radially outward deflection of the plurality of sheath removal beams during insertion of the medicament container with the protective needle sheath into the case.

11. The sheath removal mechanism according to claim 9, further comprising a portion of a needle shroud, the portion adapted to radially outwardly support the plurality of sheath removal beams to prevent radially outward deflection of the plurality of sheath removal beams during movement of the cap away from the case.

12. The sheath removal mechanism according to claim 11, wherein the portion is adapted to allow radially outward deflection of the plurality of sheath removal beams during insertion of the medicament container with the protective needle sheath into the case.

13. The sheath removal mechanism according to claim 11, wherein one or more of the plurality of sheath removal beams, a proximal face of the portion, or the internal casework are ramped for radially inwardly deflecting the plurality of sheath removal beams during removal of the cap from the case.

14. The sheath removal mechanism according to claim 9, wherein one or more of the plurality of sheath removal beams or the internal casework are ramped for radially inwardly deflecting the plurality of sheath removal beams during removal of the cap from the case.

15. The sheath removal mechanism according to claim 1, wherein the plurality of inward ledges is adapted to engage proximally behind a proximal end of the protective needle sheath or into a lateral recess within the protective needle sheath.

16. The sheath removal mechanism according to claim 1, further comprising a ramp on one or more of the plurality of sheath removal beams for engaging the protective needle sheath in a manner to radially outwardly deflect the plurality of sheath removal beams during insertion of the protective needle sheath.

17. The sheath removal mechanism according to claim 1, wherein the plurality of inward ledges provides a clearance between the plurality of inward ledges sufficiently wide to allow the protective needle sheath to pass therethrough when the plurality of sheath removal beams is in a relaxed state, and wherein one or more snap fits are respectively arranged on the plurality of sheath removal beams in a manner such that the one or more snap fits engage one another to secure neighbouring beams of the plurality of sheath removal beams to each other when the plurality of sheath removal beams is deflected radially inward.

18. The sheath removal mechanism according to claim 17, wherein the sheath removal mechanism is configured such that a needle shroud of the medicament delivery device deflects the plurality of sheath removal beams radially inward when being moved in a proximal direction.

19. An arrangement comprising:
   an assembly tool; and
   a medicament delivery device comprising a sheath removal mechanism for removing a protective needle sheath from a medicament container that is arranged in the medicament delivery device, the sheath removal mechanism comprising:
      a cap attachable to a distal end of the medicament delivery device,
      wherein the cap comprises a plurality of sheath removal beams and a plurality of inward ledges respectively arranged on the plurality of sheath removal beams and adapted to engage the protective needle sheath,
      wherein the cap defines one or more openings arranged on a distal-most face of the cap and configured to allow insertion of the assembly tool, and
      wherein the cap defines an outer surface configured to be touched by a user for removing the cap from the distal end of the medicament delivery device.

* * * * *